United States Patent

Kletschka

[11] Patent Number: 5,470,208
[45] Date of Patent: Nov. 28, 1995

[54] FLUID PUMP WITH MAGNETICALLY LEVITATED IMPELLER

[76] Inventor: Harold D. Kletschka, 1925 Noble Dr., Minneapolis, Minn. 55422

[21] Appl. No.: 990,985

[22] Filed: Dec. 16, 1992

Related U.S. Application Data

[63] Continuation-in-part of Ser. No. 774,034, Oct. 7, 1991, Pat. No. 5,195,877, which is a continuation-in-part of Ser. No. 593,695, Oct. 5, 1990, Pat. No. 5,055,005.

[51] Int. Cl.⁶ .................. F04B 17/03; A61M 1/10
[52] U.S. Cl. ............... 417/356; 417/423.7; 417/423.12; 415/900; 600/16; 623/3
[58] Field of Search ................. 417/355, 356, 417/410 R, 420, 414, 423.1, 423.7, 423.12; 415/900; 600/16; 604/151; 623/3

[56] References Cited

U.S. PATENT DOCUMENTS

| | | | |
|---|---|---|---|
| 2,747,512 | 5/1956 | Fouche | 417/356 |
| 3,575,536 | 4/1971 | Jacobs et al. | 417/420 |
| 3,597,022 | 8/1971 | Waldron | 310/90.5 |
| 3,611,815 | 10/1971 | Fischell | 310/90.5 |
| 3,647,324 | 3/1972 | Rafferty et al. | 417/420 |
| 4,340,260 | 7/1982 | Forster et al. | 310/90.5 |
| 4,408,966 | 10/1983 | Maruyama | 417/356 |
| 4,507,048 | 3/1985 | Belenger et al. | 415/900 |
| 4,642,036 | 2/1987 | Young | 417/420 |
| 4,688,998 | 8/1987 | Olsen et al. | 417/356 |
| 4,876,492 | 10/1989 | Lester et al. | 417/356 |
| 4,944,748 | 7/1990 | Bramm et al. | 623/3 |
| 5,078,741 | 1/1992 | Bramm et al. | 623/3 |
| 5,112,200 | 5/1992 | Isaacson et al. | 417/356 |

*Primary Examiner*—Richard A. Bertsch
*Assistant Examiner*—Roland G. McAndrews, Jr.
*Attorney, Agent, or Firm*—Dorsey & Whitney

[57] ABSTRACT

A fluid pump with a rotary impeller is disclosed which comprises an electromagnetically-driven, bearing-free, seal-free rotary impeller levitated by localized opposed, magnetic forces and by fluid forces, or by localized opposed magnetic forces only. Levitation by localized opposed magnetic forces alone or by a combination of magnetic and fluid forces of an impeller driven by electromagnetic forces eliminates the need for bearings and seals in the driving mechanism. This avoids the heat build-up and leakage associated with other pumping mechanisms, which can be of importance in pumping of physiological fluids such as blood. The levitating forces of the present invention are applied both axially and radially with respect to the impeller. The magnetic forces are provided by a combination of diamagnets or solenoids, opposed by permanent magnets, solenoids or electromagnets. The invention should be of use in numerous medical and non-medical applications where the benefits of impeller levitation by localized forces are apparent.

37 Claims, 21 Drawing Sheets

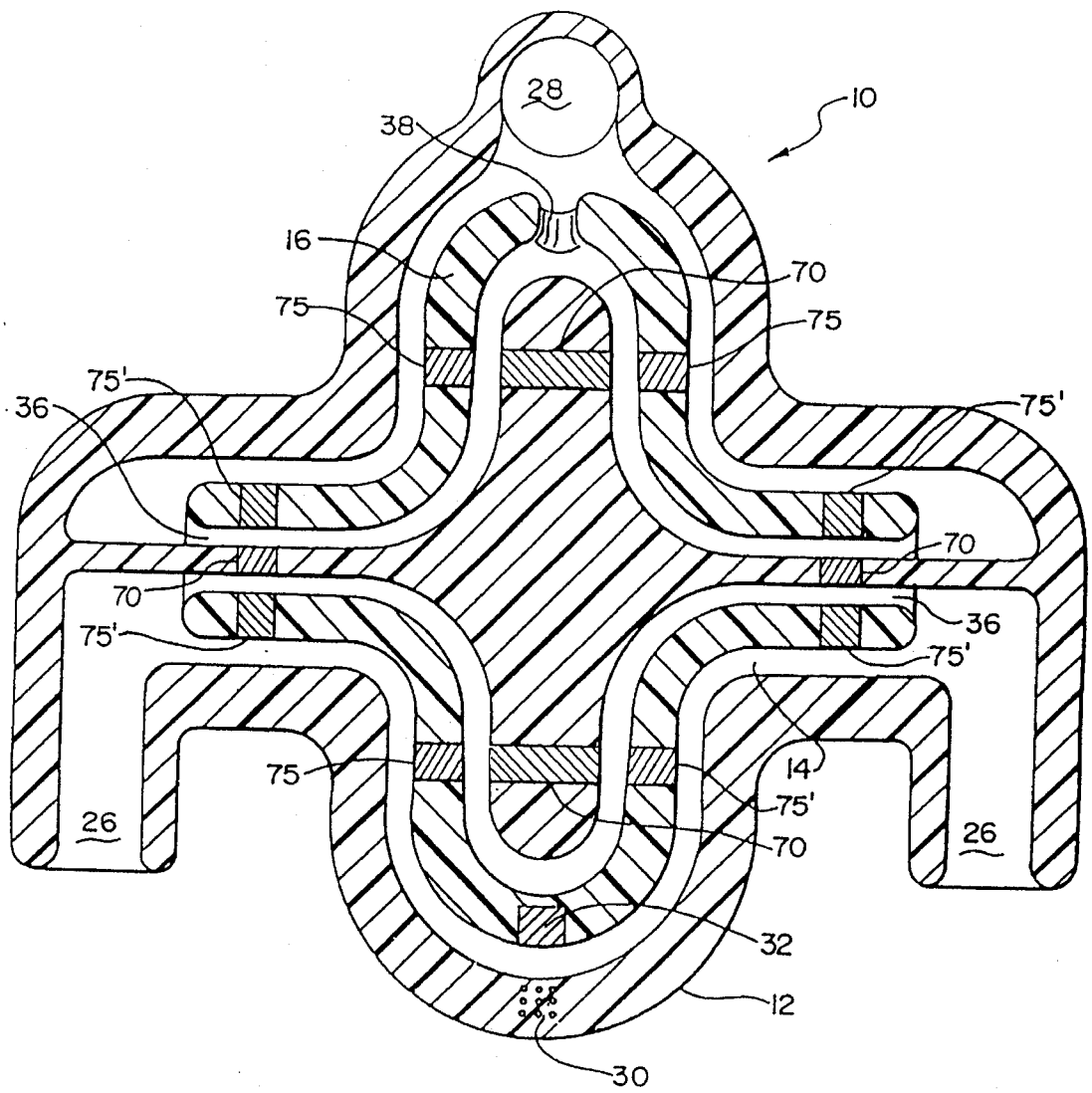

FLUID PUMP WITH MAGNETICALLY LEVITATED IMPELLER

RELATED APPLICATION

This application is a continuation-in-part of co-pending U.S. patent application Ser. No. 07/774,034, entitled Fluid Pump With Magnetically Levitated Impeller, filed Oct. 7, 1991, now U.S. Pat. No. 5,195,877 which is a continuation-in-part of U.S. patent application Ser. No. 07/593,695, entitled Fluid Pump With Levitated Impeller, filed Oct. 5, 1990, now U.S. Pat. No. 5,055,005.

BACKGROUND OF THE INVENTION

This invention relates to a fluid pump with a rotary impeller. More particularly this invention relates to a fluid pump with a bearing-free, seal-free electromagnetically-driven rotary impeller. The impeller is levitated by a combination of axial and radial localized opposed magnetic and fluid forces or by axial and radial magnetic forces only. The magnetic forces used for levitation are generated by a combination of solenoids or diamagnets and permanent magnets, electromagnets or solenoids.

Levitation of the impeller by such forces allows for high efficiency in converting power into useful work. Thus, a relatively small energy source can be used and the life of the energy source is correspondingly extended. Moreover, use of a levitated impeller driven by electromagnetic forces eliminates the need for driving mechanism bearings and seals, thereby avoiding the heat build-up and leakage attendant with other rotary pump inventions. Such considerations can be of critical importance for pumping of physiological fluids such as blood.

A large number of mechanisms for pumping fluids have been described in the art, including, for example, peristaltic pumps, moving diaphragm pumps, piston-type pumps, and centrifugal or rotary pumps. Generally, a rotary pump includes a pumping chamber with inlet and outlet ports and an impeller mounted within the pumping chamber for rotation about an axis. Frequently the impeller is mounted on a shaft that extends through one or more seals and a bearing apparatus to a rotational driving mechanism outside the pumping chamber. Rotary pumps employing shaft-mounted impellers with shaft seals are exemplified in the following U.S. patents: Dorman et al. U.S. Pat. No. 3,608,088; Rafferty et al. U.S. Pat. No. 3,647,324; Reich et al. U.S. Pat. No. 4,135,253; Clausen et al. U.S. Pat. No. 4,589,822; Moise U.S. Pat. No. 4,704,121; and Kletschka U.S. Pat. No. 4,844,707. Shaft seals are susceptible to wear and heat build-up, which can lead to leakage and, in the case of blood pumps, to thrombogenic (clot-forming) problems, denaturation of proteins, and embolic phenomena and the like.

Other pump inventions employ liquid or hydrostatic bearings to reduce heat build-up and/or to dissipate heat and to reduce frictional forces in rotation of the shaft and/or impeller. In these inventions liquid or gas is forced into narrow clearances between the shaft and various bearing assemblies or between the impeller and the impeller housing. The relatively thin fluid or gas films generated in these inventions are nevertheless subject to high shear forces and some incremental heat build-up. The following U.S. patents exemplify the use of such liquid or hydrostatic bearings: Prindle U.S. Pat. Nos. 845,816 and 888,654; Anderson U.S. Pat. No. 2,864,552; Baker et al. U.S. Pat. No. 3,122,101; and Kambe et al. U.S. Pat. No. 4,475,866.

Olsen et al. U.S. Pat. No. 4,688,998 discloses a fluid pump with an electromagnetically driven and levitated impeller. In Olsen et al., a sensor and a controller are provided to sense and control the amount of electromagnetic levitating force applied to the impeller. Only electromagnetic levitating forces are applied to the impeller. Unlike the present invention, in Olsen et al. the levitational forces are provided by electromagnets. In addition, in Olsen et al. the levitational forces are not applied to the impeller in separate and distinct axial and radial directions.

In the fluid pump disclosed in U.S. Pat. No. 5,055,005, which is the grand parent of this application, while all the input energy is directed to rotation of the impeller, a portion of the output energy from the peripheral region of the impeller (which includes locations downstream from the periphery of the impeller) is diverted for use in levitating the impeller by fluid force. Thus, not all of the input energy is directed toward pumping fluid from the pump. The fluid pump disclosed in U.S. Pat. No. 5,195,877, which is the parent of this application is an improvement on the aforementioned fluid pump. In the fluid pump disclosed in U.S. Pat. No. 5,195,877, the impeller is levitated and positioned in the fluid pump by auto-adjusting, permanent repulsive magnetic forces. This makes it possible for more input energy to be directed to rotation of the impeller and pumping of the fluid. The embodiment disclosed herein improves on the fluid pump disclosed in U.S. Pat. No. 5,195,877 and employs a combination of permanent magnets, solenoids, electromagnets or diamagnets to levitate and position the impeller in the fluid pump.

SUMMARY OF THE INVENTION

In accordance with the present invention, a rotary pump is disclosed which is comprised of a housing defining a pumping chamber with one or more pumping chamber inlet ports and one or more pumping chamber outlet ports; a rotatable impeller or impellers disposed in the pumping chamber for rotation about an axis; polarized electromagnetic means for rotating the impeller about the axis; and opposed magnetic means located in the housing and impeller, respectively, such as a combination of diamagnets or solenoids in the housing opposed by permanent magnets, solenoids or electromagnets in the impeller for levitating the impeller axially, radially or both.

In the case of magnetic levitation of the impeller in the axial direction only or in the radial direction only, levitational forces in the other direction can be provided by fluid forces conducted from the peripheral region downstream of the impeller. Means is provided for conducting fluid from a high pressure area at the peripheral region of the impeller and for discharging the fluid in opposed directions within a lower pressure area in general proximity to the axis of the impeller, in either an axial or radial direction. Thus the impeller is thereby levitated and stabilized within the pumping chamber by application of axial and/or radial fluid forces in combination with magnetic forces in the axial and/or radial direction.

The impeller may be fashioned of various materials, preferably nonmagnetic such as methyl methacrylate. Preferably, the impeller has an overall bulk density similar or identical to that of the fluid being pumped. This results in suspension of the impeller in the pumped fluid and facilitates levitation and stabilization of the impeller within the pumped fluid.

The impeller may take various shapes, and may or may not have vanes, depending upon the particular pump application. The impeller may be solid, or may have internal fluid-filled space in communication with the pumping chamber or with the pumping chamber inlet and/or outlet ports. The impeller may have a single inlet or opposed inlets near the axis of the impeller communicating with the pumping chamber inlet ports, and opposed outlets at the periphery of the impeller communicating with the pumping chamber outlet port or ports. The impeller preferably has axially extending neck portions.

Magnetic stabilization or levitation is achieved by magnetic forces in balanced opposed axial and/or radial directions. A plurality of magnet means is preferably located in the housing in magnetic communication with a plurality of magnet means located in the impeller. These magnet means are arranged both axially and radially with respect to the impeller for magnetic stabilization both axially and radially. The magnet means may also be arranged only axially or only radially for magnetic stabilization in only the axial direction or in only the radial direction, in which case stabilizing forces in the other direction can be provided by fluid forces.

In one embodiment, the housing comprises a central frame about which the impeller rotates. Magnet means may be placed in this central frame so as to be in magnetic communication with the magnet means located in the impeller.

The magnetic forces are provided by a combination of, diamagnets or solenoids, opposed by permanent magnets, electromagnets or solenoids. The opposing magnet means may be disposed with the polarity of the opposing forces oriented to either repel or attract. Balanced repulsive magnetic forces are preferred when one of the magnet means is a diamagnet. Either balanced attractive magnetic forces or balanced repulsive forces may be used when one of the magnet means is a solenoid. If a diamagnet and a solenoid are used in combination, preferably balanced repulsive magnetic forces are used. When solenoids are used to provide the magnetic flux, sensors and a control system are required to control the amount of electricity sent through the coils of the solenoid to vary the magnetic flux.

In the case of magnetic stabilization in one direction (axially or radially) only, stabilizing forces in the other direction (radially or axially) can be provided by means of conduits emanating from the vicinity of the pumping chamber outlet port and terminating in various configurations generally near the axially extending neck portion of the impeller which conduct fluid forces to the impeller for impingement on the impeller. Thus, magnetic forces, or fluid forces together with magnetic forces, cause levitation of the impeller.

Polarized electromagnetic means for rotating the impeller may comprise electrically conductive wire windings within the periphery of the pump housing electromagnetically coupled to permanent magnets housed within the periphery of the impeller. Alternatively, the polarized electromagnetic means for rotating the impeller may comprise electrically conductive wire windings housed within a stator located internal to the impeller, the stator being in structural communication with the pump housing and electromagnetically coupled to one or more magnets housed within the internal structure of the impeller.

As used herein the term "fluid" means any aggregate of matter in which the molecules are able to flow past each other without limit and without the formation of fracture planes. The term includes gases, liquids, solutions, suspensions, slurries and gels and includes such specific substances as blood, plasma and serum.

BRIEF DESCRIPTION OF THE DRAWINGS

The above and other objects and advantages of this invention will be apparent upon consideration of the following detailed description, taken in conjunction with the accompanying drawings, in which:

FIGS. 14A–M show various embodiments of the present invention.

DETAILED DESCRIPTION OF THE INVENTION

The preferred application of pumps of the present invention is in the medical field for pumping blood. However, the pumps of the present invention may be used in other medical and non-medical pumping applications. Where pumps are to be used as artificial hearts they must be able to pump adequate amounts of blood ranging in rate from 6 to 26 liters of blood per minute, to span the range for an average adult male to that of a well conditioned athlete. The pumps of the present invention meet this criteria with rotation of the impeller typically at speeds in the range of 2000 to 4000 rpm. Speeds may be lower or higher, however, depending on pump and impeller size and configuration and application.

Figure 1:
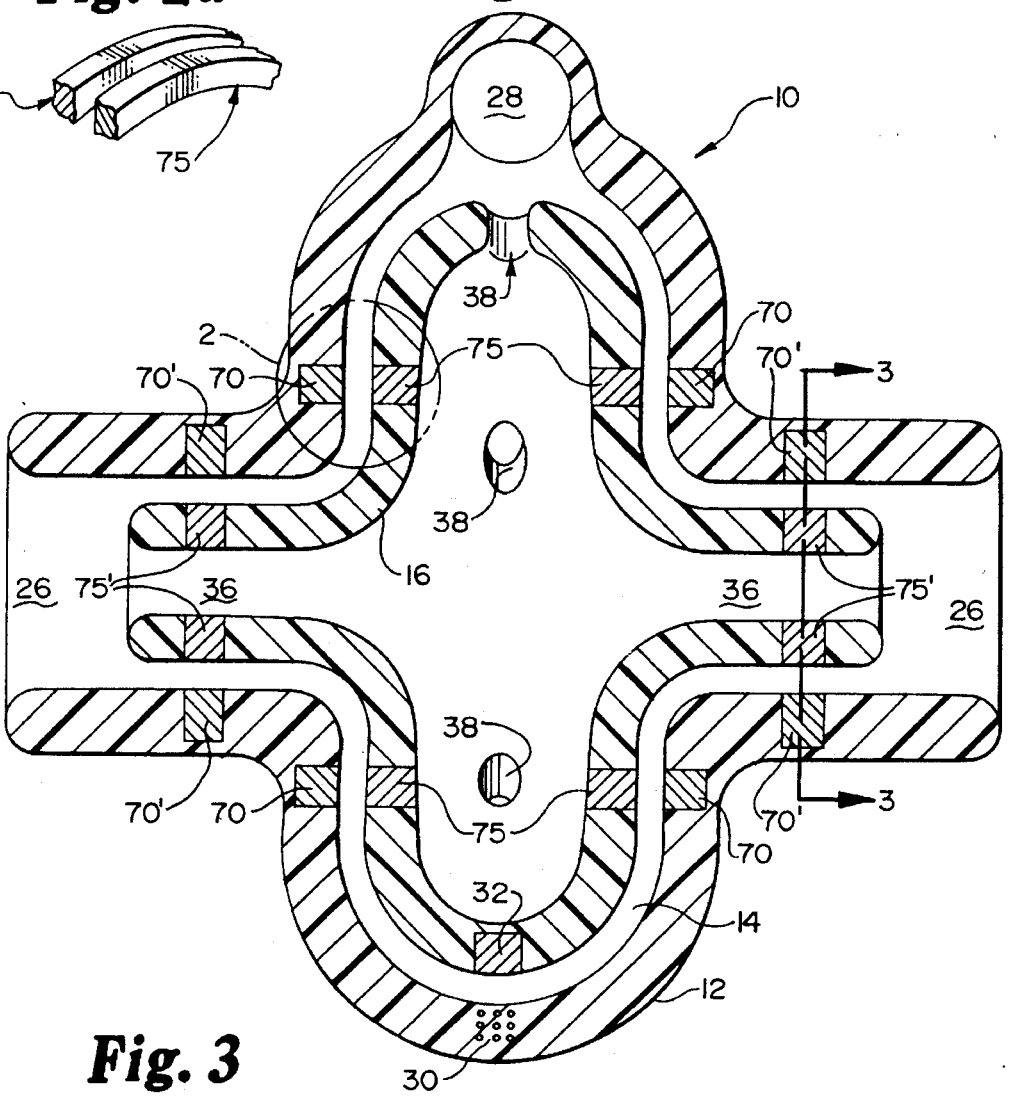
FIG. 1 is an axial sectional view of a preferred embodiment of the present invention where axial and radial levitation is achieved solely by opposed magnetic forces.

FIG. 1 depicts a preferred embodiment of the pump 10 of the present invention. Pump 10 comprises a pump housing 12 defining inlet ports 26, a pumping chamber 14 through which fluid is pumped, outlet port 28, and an impeller 16. Pump housing 12 may be fashioned from two or more component parts secured together with fasteners.

The embodiment depicted in FIG. 1 has two inlet ports 26 and a single outlet port 28. However, housing 12 could be reconfigured to define a single inlet port or more than two inlet ports and/or multiple outlet ports. Other configurations of inlet ports and outlet ports for various applications of this invention will be apparent to those skilled in the art. See for example FIGS. 5 and 6.

The periphery of pump housing 12 incorporates electromagnetic wire windings 30 for rotating impeller 16 about the impeller axis. One embodiment of the electromagnetic wire windings is shown in U.S. Pat. No. 5,055,005, the disclosure of which is hereby incorporated by reference. Wire windings 30 are electromagnetically coupled to permanent magnets 32 housed within and spaced about the peripheral structure of impeller 16.

Wire windings 30 may alternatively be incorporated into a stator located interior to impeller 16, and about which impeller 16 may rotate, such as shown in FIG. 20 of U.S. Pat. No. 5,055,005. The stator may be supported within impeller 16 by one or more supporting shafts disposed along the axis of rotation of impeller 16, the shafts being in structural communication with pump housing 12. Wire windings 30 within the stator may be in electrical communication with one or more electrical power sources by means of wires running from the stator through the supporting shafts to one or more of such electrical power sources located within or external to pump 10. Other configurations of electromagnetic means for rotating impeller 16 about an axis will be obvious to those skilled in the art.

Impeller 16 has opposed inlets 36 in fluid communication with inlet ports 26. Impeller 16 also has outlets 38 at the periphery of impeller 16 in fluid communication with outlet port 28. Fluid enters pump 10 at inlet ports 26 and proceeds to inlets 36.

Acceleration is imparted to the fluid due to shear forces operating between the interior walls of impeller 16 and the fluid as impeller 16 rotates, and between the molecules and particles of the fluid. Fluid exiting outlets 38 due to centrifugal forces operating within the accelerated fluid imparts circumferentially and radially directed fluid forces to the fluid within pumping chamber 14. Similarly directed fluid forces are generated by frictional shear forces operating between the outer surfaces of impeller 16 and the fluid and between the molecules and particles of the fluid. Fluid thus enters pump 10 at inlet ports 26 and exits at outlet ports 28.

For biological or medical applications, it would be useful, but not necessary, for impeller 16 to be of a density similar or identical to that of the fluid being pumped. However, in any application and regardless of the density of impeller 16, it is only necessary that the levitating forces be sufficient to counteract gravitational and inertial forces acting on impeller 16. Biological and medical uses of the invention could include both human and veterinary applications. Similarly, the invention could be employed to function ex vivo (outside the body) or in vivo (inside the body), as well as in biological or non-biological and medical or non-medical uses not connected to a human or animal body.

Magnetic forces may be used for both radial and axial stabilization of impeller 16. A combination of diamagnets or solenoids, opposed by permanent magnets, electromagnets or solenoids may be used in pump housing 12 and impeller 16, respectively.

Diamagnets are substances that have a magnetic permeability less than one. They are repelled by a magnetic force. Examples of diamagnets include alkali and alkaline earth metals, ceramics, bismuth, gold, graphite, copper oxide, superconductors and the halogens and noble gases. Examples of superconductors include fullerenes, a special configuration of the carbon 60 or carbon 70 molecule composed of hexagonal rings and pentagonal rings. As used herein the term "diamagnet" means any substance that possesses diamagnetic properties either inherently or induced therein such as by electrical field or current, and includes all of the examples given above.

A solenoid is a coil of wire carrying an electric current. Any appropriate power source may be used to provide the electric current. The current may be A.C. or D.C. and may be continuous or intermittent. The wire can be made from any electrically conductive material including superconducting material. A solenoid has the properties of a magnet but differs from an electromagnet which includes a magnetizable core such as soft iron. A solenoid is more efficient than an electromagnet because the introduction of a piece of iron into a solenoid decreases the effective magnetizing power of the coil.

Although solenoids can be made in a variety of shapes, preferably a helical (see FIG. 2b) or toroidal (see FIG. 2c) solenoid is used. A solenoid of customary disc configuration may also be used. It should also be recognized that a combination or composite of such solenoid configurations could also be used. Such solenoids are compact and can be fitted into housing 12 or impeller 16 immediately adjacent to the surface. Thus any heat generated by the solenoid can be quickly dissipated by the rapidly moving fluid pumped through pump 10.

By using diamagnets or solenoids in combination with permanent magnets, electromagnets or solenoids, the effects of Earnshaw's theorem can be avoided. Earnshaw's theorem states that in a non-dynamic system composed solely of permanent magnets, it is impossible for a body to be supported in stable equilibrium against displacements in all directions. However, diamagnets and/or solenoids can be used in combination with permanent magnets, electromagnets or solenoids to achieve stable equilibrium.

In the preferred embodiment of FIG. 1, a plurality of magnet means 70 located in pump housing 12 is in magnetic communication with a plurality of magnet means 75 located in impeller 16. At least one magnet means 75 should be located in impeller 16 in the axial direction and be in magnetic communication with at least one magnet means 70 located in housing 12. Preferably one magnet means 70' in housing 12 has an annular shape and surrounds magnet means 75' in impeller 16. This arrangement stabilizes impeller 16 in the radial direction. See FIG. 3. In addition, a magnet means 75 is located along the radial axis in impeller 16. Preferably one magnet means 75 is located on each side of impeller 16. These magnet means are in magnetic communication with magnet means 70 in housing 12. This arrangement stabilizes impeller 16 in the axial direction. See

FIG. 2a.

Magnet means 70 and 75 comprise first means for generating a magnetic force and magnet means 70' and 75' comprise second means for generating a magnetic force disposed in opposing magnetic communication. Magnet means 70 and 70' are fixed with respect to housing 12. Magnet means 75 and 75' are fixed with respect to impeller 16. Together they comprise first and second magnetic means with either constituting the first magnetic means and the other constituting the second magnetic means. First magnetic means 70 or 75 is selected from the group consisting of diamagnets and solenoids. Second magnetic means 75 or 70 is selected from the group consisting of permanent magnetics, solenoids and electromagnets, and is disposed in opposing magnetic communication with the first magnetic means 70 or 75, to thereby stabilize impeller 16 by levitating magnetic forces.

When diamagnets are used as magnet means 70 or 75, they will always repel the polarity of the opposing permanent magnets, electromagnets or solenoids. On the other hand, when solenoids are used as magnet means 70 or 75, they can be arranged so that the opposing second means for generating a magnetic force is disposed with its polarity oriented to repel or attract. In addition, when solenoids are used as magnet means 70 or 75, a suitable sensor and control means must be used in conjunction with the solenoids to ensure that impeller 16 remains levitated and in equilibrium. Such a sensor means can determine when impeller 16 becomes unbalanced. This sensor means can then signal the control means which in turn increases or decreases the current to one or more of the solenoids. This adjusts the magnitude of the magnetic flux to urge impeller 16 back into equilibrium. A control circuit as described in Bramm et al., U.S. Pat. No. 4,944,748 can be used by one of ordinary skill in the art to provide the needed controls for this invention.

Figure 2A:
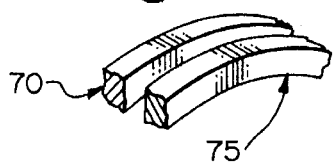
FIG. 2a is a cut-away view of the preferred embodiment of the present invention, showing the orientation of one set of magnetic means in the housing and impeller, respectively, to provide axial levitation, taken in the region 2 shown in FIG. 1.
Figure 3:
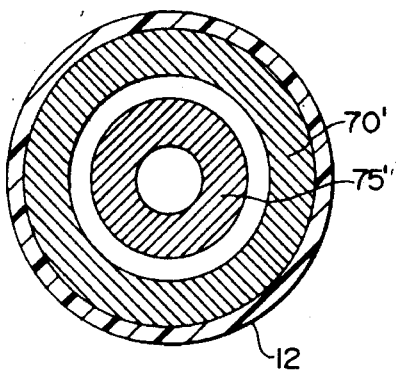
FIG. 3 is a cross-sectional view of the preferred embodiment of the present invention, taken on line 3—3 of FIG. 1 showing the orientation of another set of magnetic means in the housing and the impeller to provide radial levitation.

As shown in FIGS. 2a and 3, magnet means 75 in impeller 16 and magnet means 70 in pump housing 12 are arranged so that they remain in magnetic communication with one another. Although as shown, each set of magnet means 70 and 75 comprises only one magnet means 75 in impeller 16 and one magnet means 70 in housing 12, any number of magnet means 70 and 75 in housing 12 and impeller 16 can be used to provide the axial and radial levitation for impeller 16. The only limitation on the number of magnet means 70 and 75 used in a particular set is that the magnetic flux emanating from magnet means 70 in housing 12 must always be in magnetic communication with the magnetic flux emanating from magnet means 70 in impeller 16 or vice versa.

Figure 4:
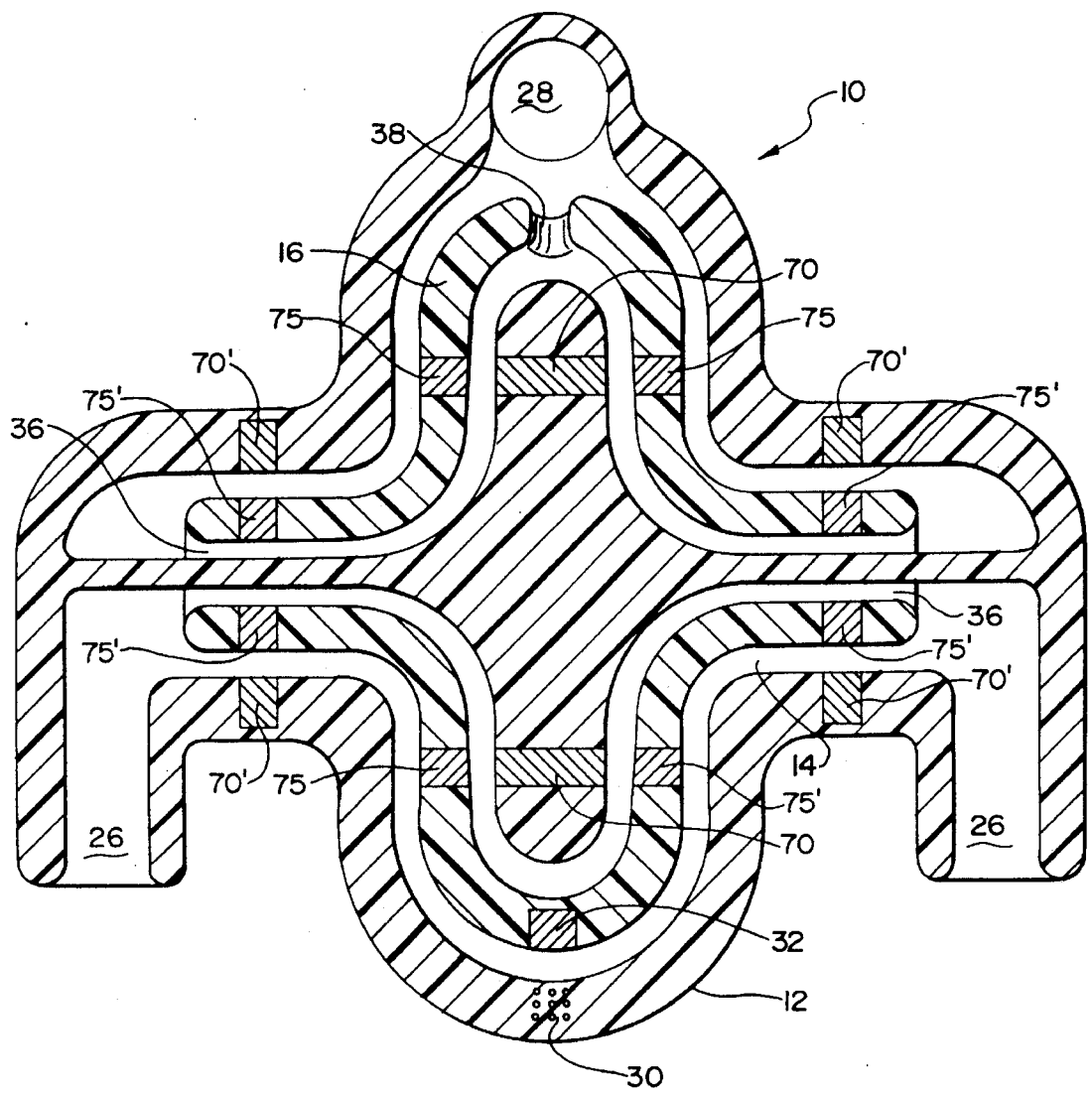
FIG. 4 is an axial sectional view of another embodiment of the present invention characterized by a central frame, where axial and radial levitation is achieved solely by opposed magnetic forces.

FIG. 4 depicts another embodiment of the pump of the present invention. In this embodiment, housing 12 includes a central frame about which impeller 16 rotates. Magnet means 70 may be placed in this central frame to provide axial stabilization. If magnet means 70 located in this central frame is a diamagnet, two such diamagnets must be used on either side of the central frame rather than just one as shown.

Figure 5:
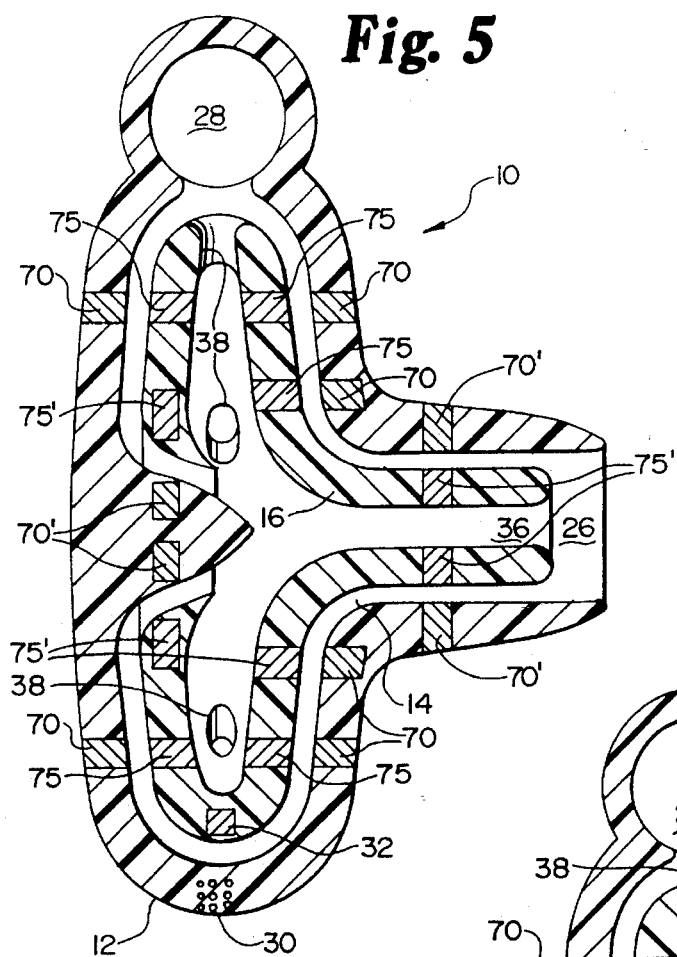
FIGS. 5 and 6 are axial sectional views of additional embodiments of the present invention, characterized by a single inlet pumping chamber, where axial and radial levitation is achieved solely by opposed magnetic forces.
Figure 6:
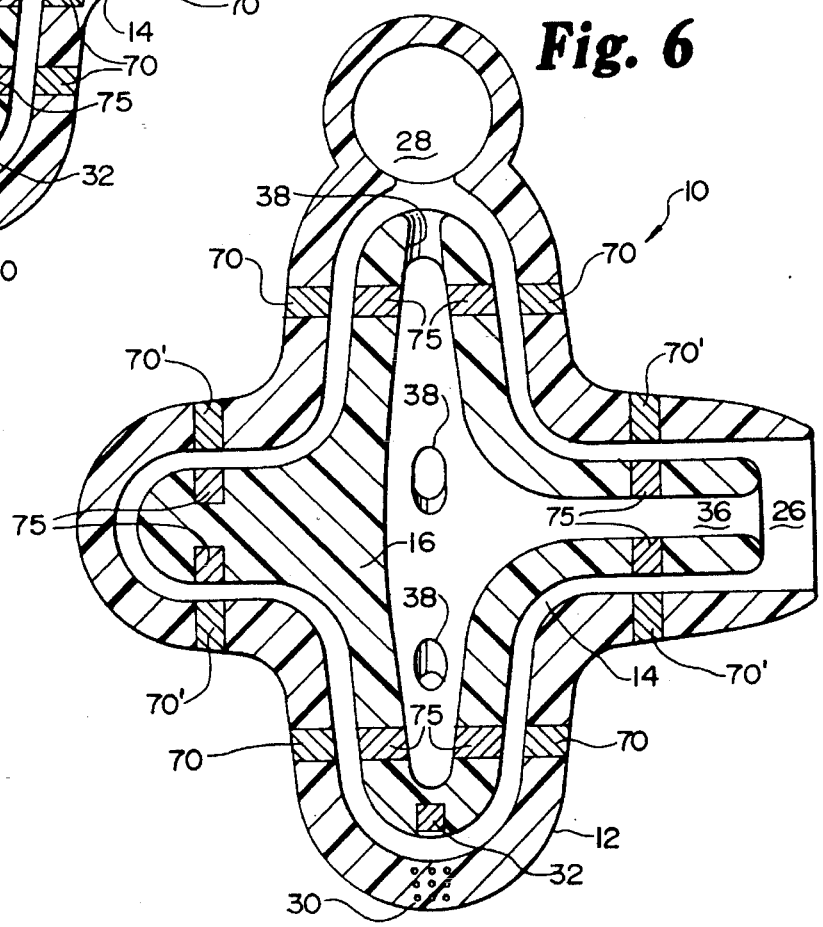

FIGS. 5 and 6 depict alternative embodiments characterized by a housing 12 that defines a single pumping chamber inlet 26 and a non-symmetrical impeller 16. The rest of the elements or components shown in FIGS. 5 and 6 correspond to the commonly designated elements or components shown in FIGS. 1–4 and described above.

Figure 7:
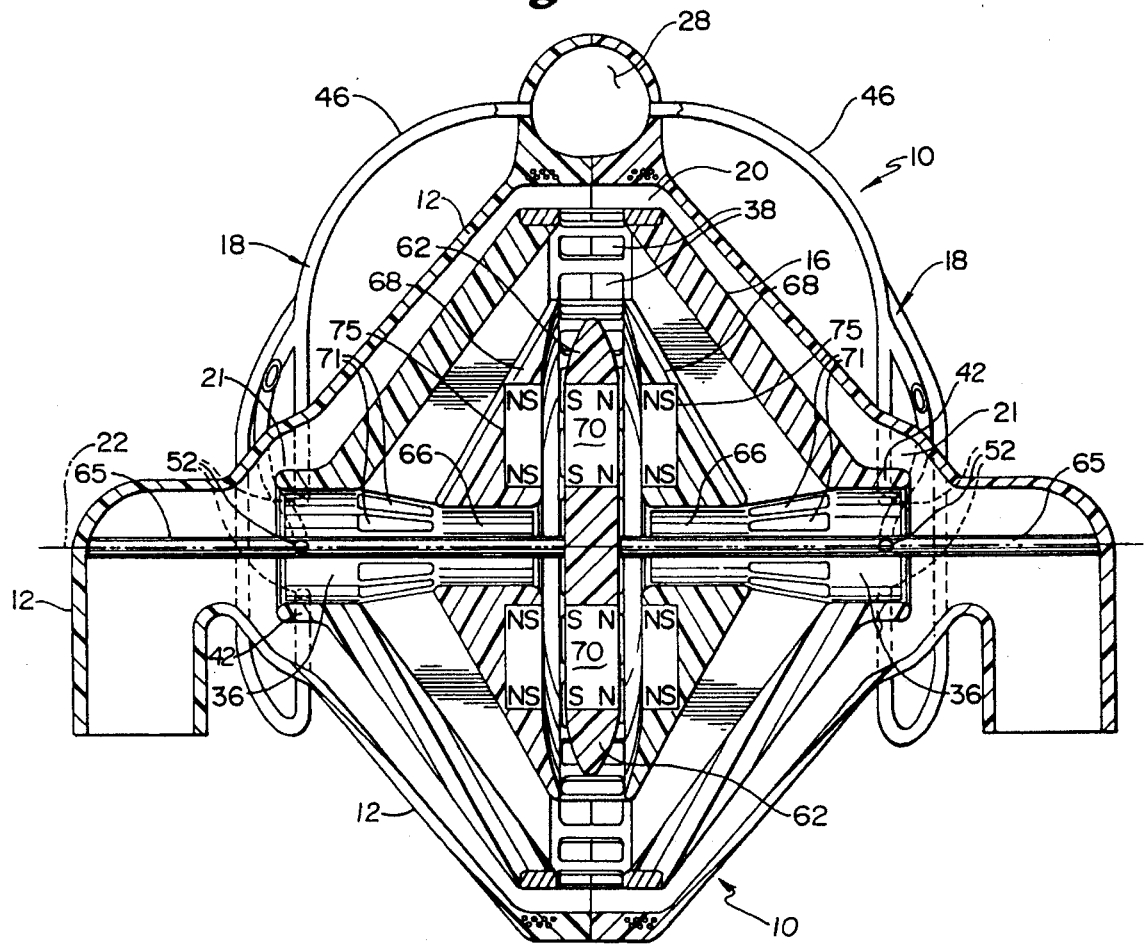
FIG. 7 is an axial sectional view of another embodiment of the present invention characterized by a central frame where axial levitation of the impeller is achieved by repulsive magnetic forces in accordance with the present invention and radial levitation is achieved by fluid forces.

FIG. 7 depicts another embodiment of the pump 10 of the present invention in which axial stabilization of the impeller is achieved by repulsive magnetic forces and radial stabilization is achieved by fluid forces. The pump includes means 18 for conducting fluid from a higher pressure region 20 near the periphery of impeller 16, including pumping chamber outlet port 28, and discharging the fluid in a lower pressure region 21 in general proximity to the axis 22 of impeller 16.

In this embodiment, impeller 16 includes opposed, axially extending neck portions 42 that encompass the opposed inlets 36. Such neck portions facilitate radial, fluid-force levitation of impeller 16 by providing appropriately directed surfaces upon which levitating fluid forces may be directed. Such neck portions may be eliminated, however, by providing functionally equivalent inwardly facing surfaces for radial fluid-force levitation, such as shown in FIGS. 9, 14, 19 and 20 of U.S. Pat. No. 5,055,005, and they may be eliminated without substitution of a functional equivalent if magnetic forces are used for radial levitation. Neck portions 42 also facilitate axial, fluid-force levitation of the impeller by providing circular concave surfaces 43, shown in FIG. 9, into which the axial fluid forces may be directed. Numerous other configurations of impeller 16, however, will be applicable to the concept embodied in the present invention—that of impeller levitation by localized forces. For example, the total frictional force exerted by impeller 16 on the fluid could be increased by providing additional partitions or walls within impeller 16 transverse to the axis of rotation.

Generally, in embodiments where the invention is used for the pumping of physiological fluids such as blood, vanes and other structures potentially capable of creating turbulence and/or excessive shear forces should be avoided. However, the invention is suitable for the pumping of any fluid (liquid or gas) where the advantages of impeller levitation by localized forces are desired, and vanes and other structures designed to increase the shear forces generated by the impeller may be useful in such embodiments. In some embodiments, the fluid forces generated solely through interaction of the fluid with the rotating outer surface of the impeller may be adequate for the intended purpose(s). In such embodiments, impeller 16 could be "solid," i.e., lacking an internal cavity in communication with the pumping chamber via impeller inlets and outlets.

Referring again to the embodiment shown in FIG. 7, radial stabilization of impeller 16 is achieved by means 18 for conducting fluid from a region of higher fluid pressure 20 near the periphery of impeller 16 and discharging in a region of lower fluid pressure 21 so as to radially stabilize impeller 16 by levitating fluid forces. Means 18 is comprised of conduits 46 emanating from pumping chamber outlet port 28. The configuration of the conduit/outlet port junction must be such that the tendency for fluid within the conduit to move toward, rather than away from, the higher pressure fluid flow region within outlet port 28, in accordance with Bernoulli's Law, is overcome. Conduit 46 may leave outlet port 28 in an orientation tangential to the direction of fluid flow within outlet port 28 in order to achieve the desired result. Alternatively, deflectors may be placed within the junction to facilitate diversion of fluid flow into conduits 46. Other configurations of the conduit/outlet port junction for overcoming adverse fluid flow dynamics due to Bernoulli's Law will be apparent to those skilled in the art.

Referring again to the embodiment shown in FIG. 7, each conduit 46 terminates in structure defining three fluid jet ports 52 within a lower fluid pressure region in inlet port 36 in general proximity to the axially extending neck portion 42 of impeller 16. The fluid jets emanating from three fluid jet ports 52 on both sides of impeller 16 define a fluid plane or circle of orientation suitable to prevent impeller 16 from moving in the radial direction so as not to touch the walls of pump housing 12 or distal ends of fluid jet ports 52. Each conduit 46 could terminate in one or more than three fluid jet ports, depending on the shape of impeller 16 and fluid flow dynamics in specific alternative embodiments of the invention, as shown for example in FIGS. 15–17 of U.S. Pat. No. 5,055,005.

In the configurations described above, and in alternative embodiments described below, the fluid jet ports are oriented such that the levitating fluid forces are auto-adjusting. That is, a change in corrective force will be automatically or inherently incurred by any attempted displacement in location of the impeller.

Figure 9:
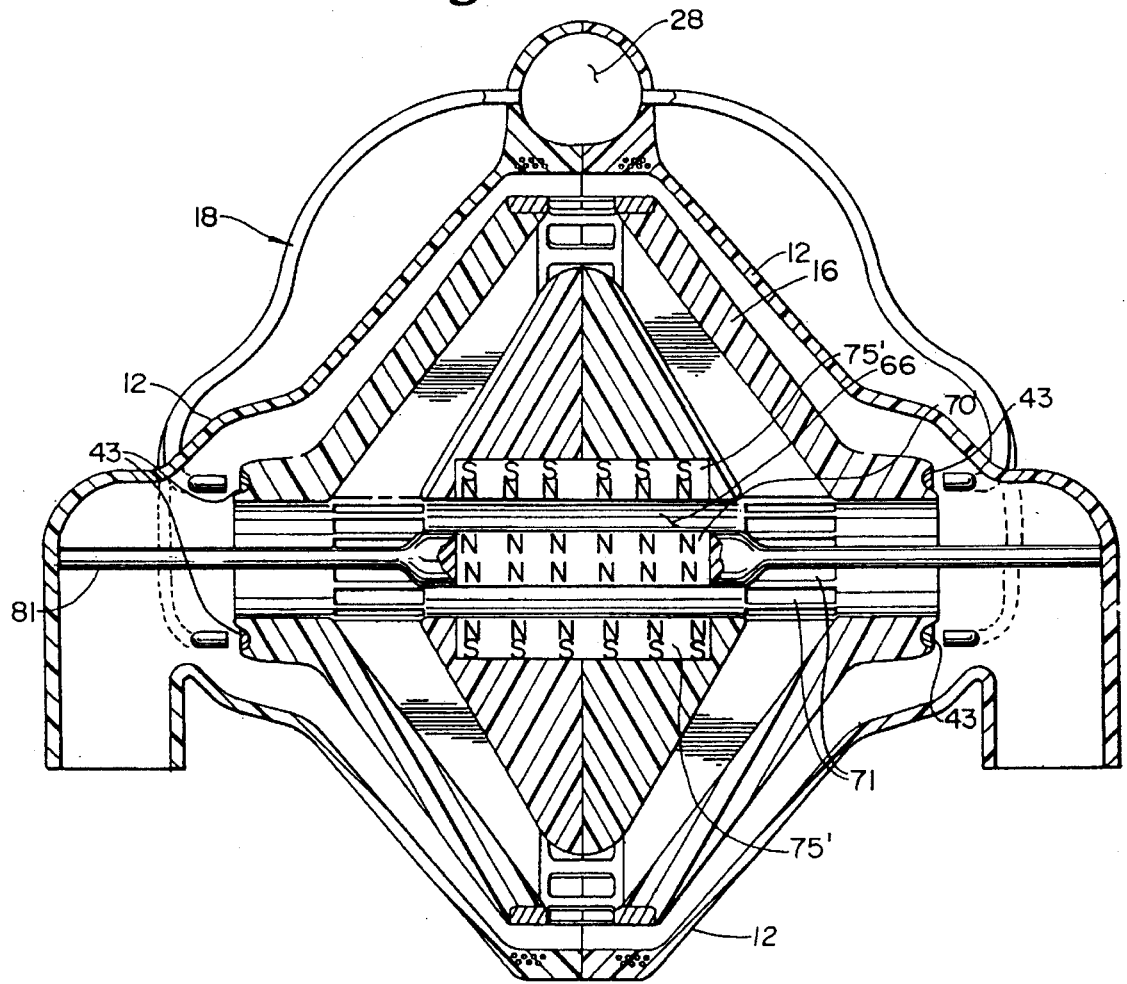
FIG. 9 is an axial sectional view of another embodiment of the present invention where radial levitation is achieved by repulsive magnetic forces in accordance with the present invention and axial levitation is achieved by fluid forces.
Figure 13:
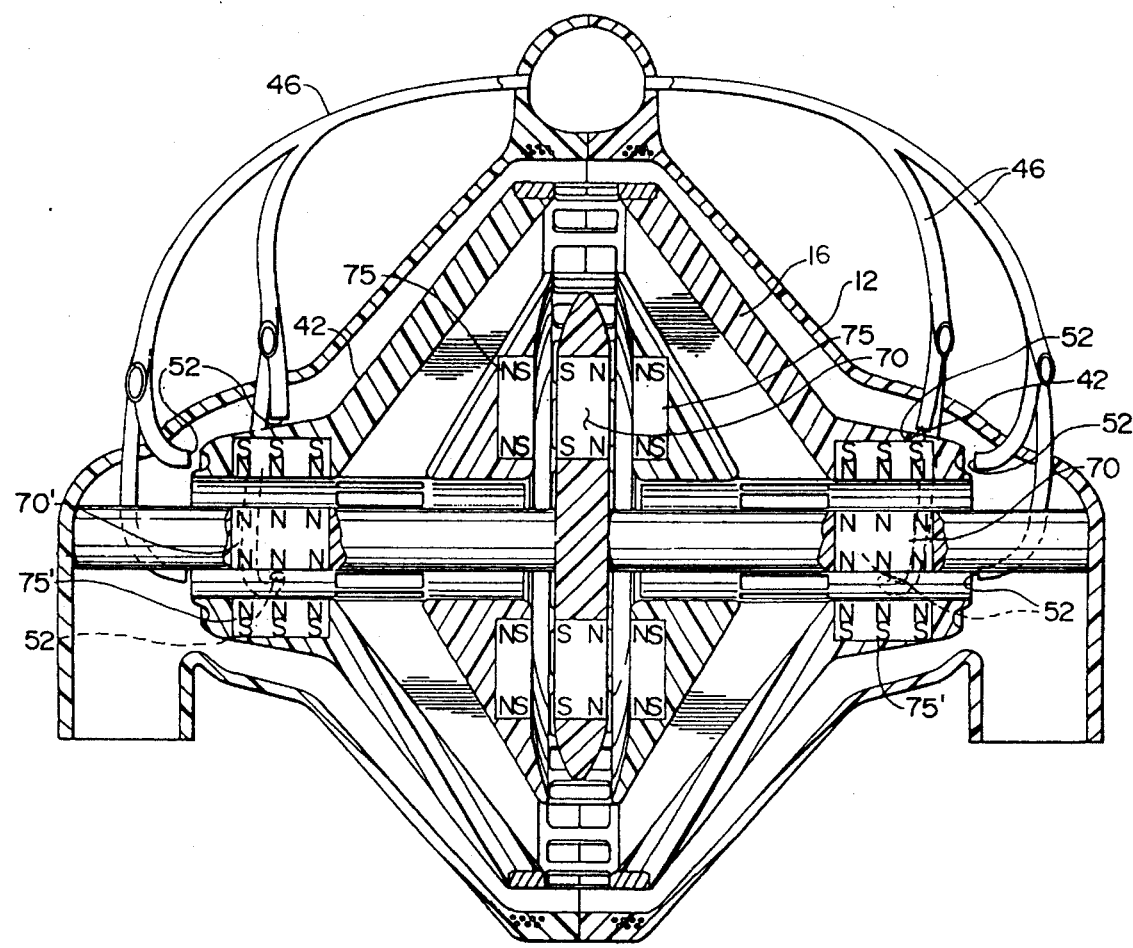
FIG. 13 is an axial sectional view of a final embodiment of the present invention where both axial and radial levitation are achieved by both magnetic forces and fluid forces. The embodiment of FIG. 13 is thus redundant in that both magnetic and fluid forces are used to levitate the impeller both axially and radially.
Figure 14A:
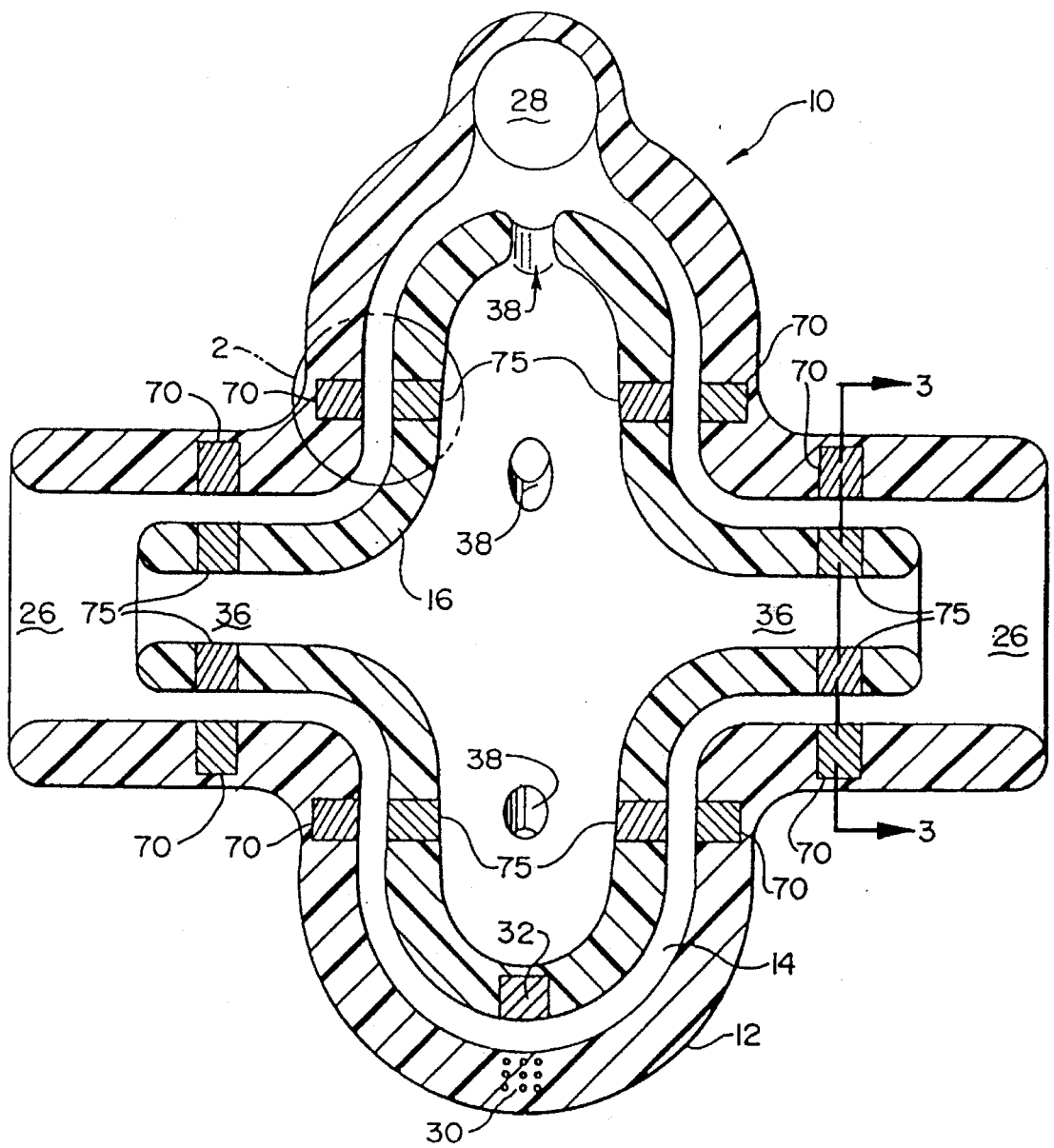
Figure 14B:
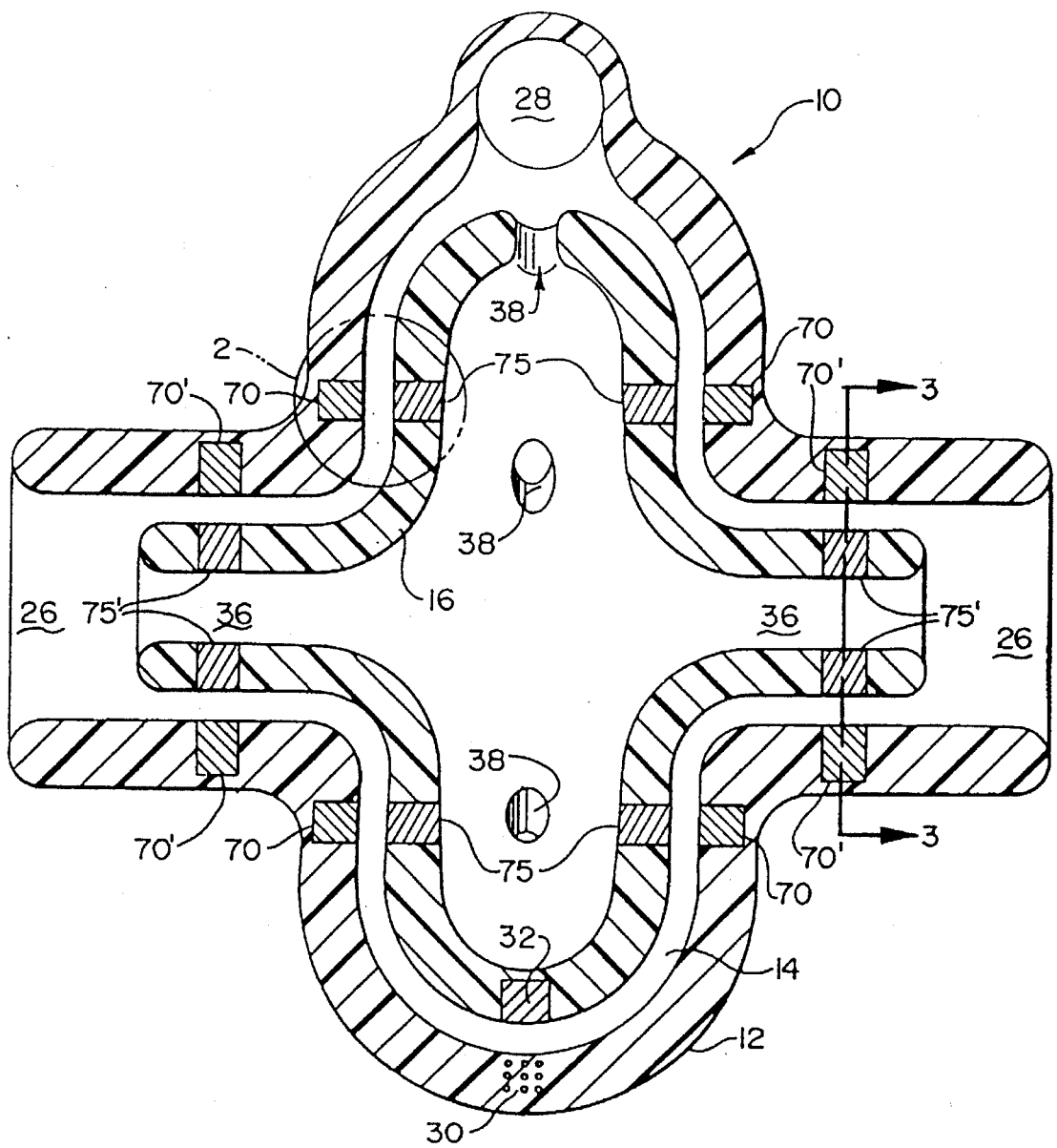
Figure 14C:
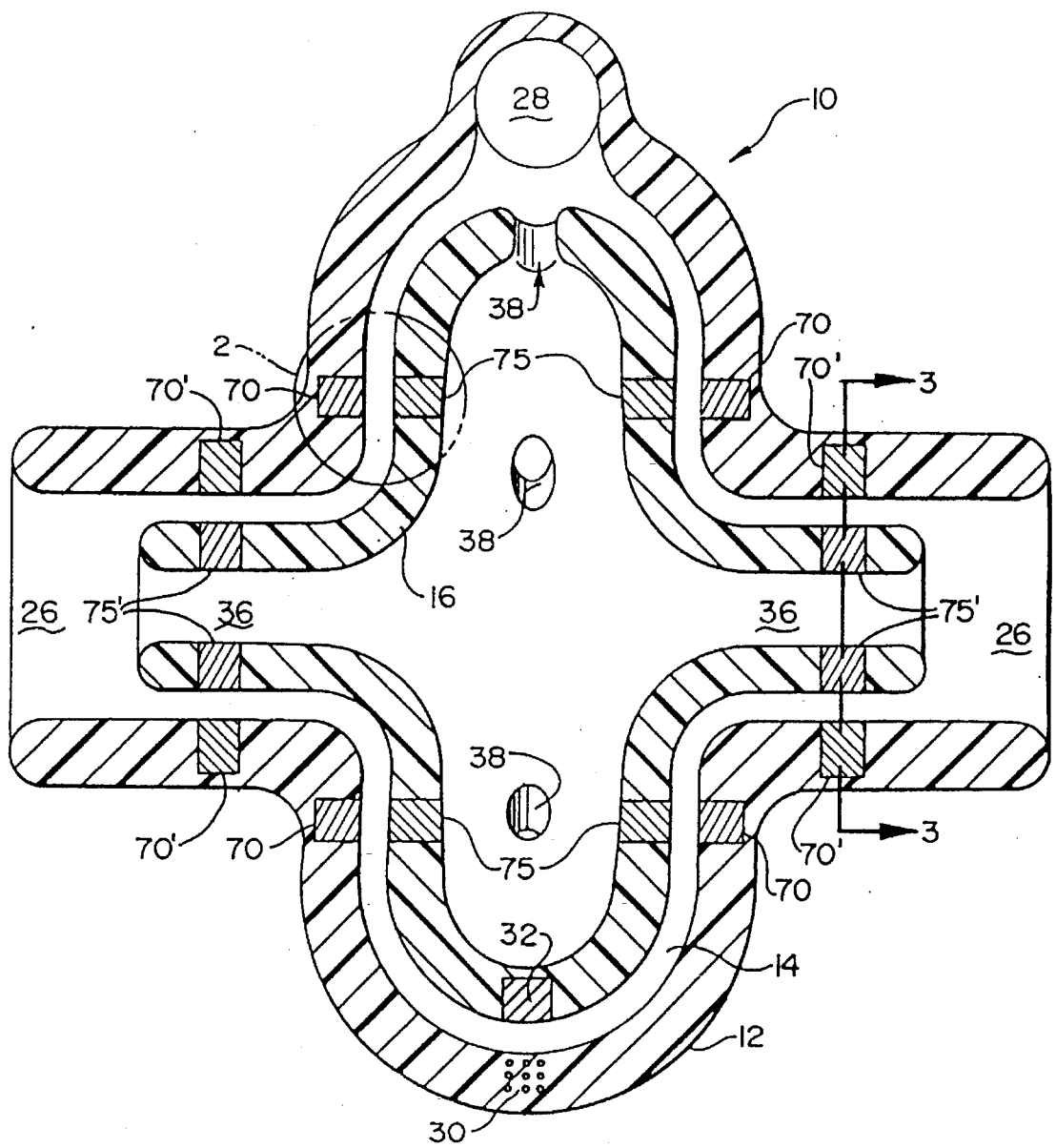
Figure 14D:
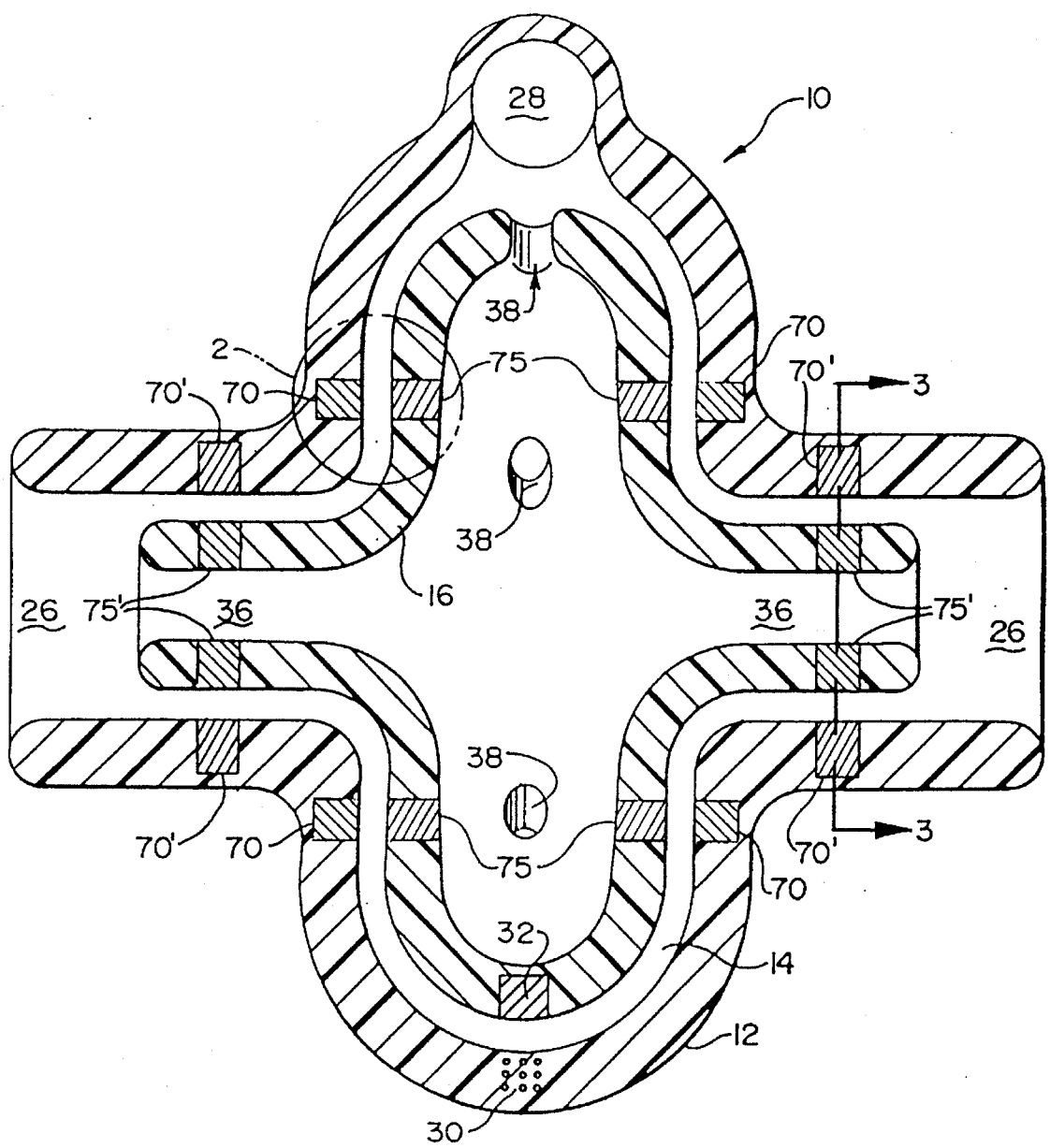
Figure 14E:
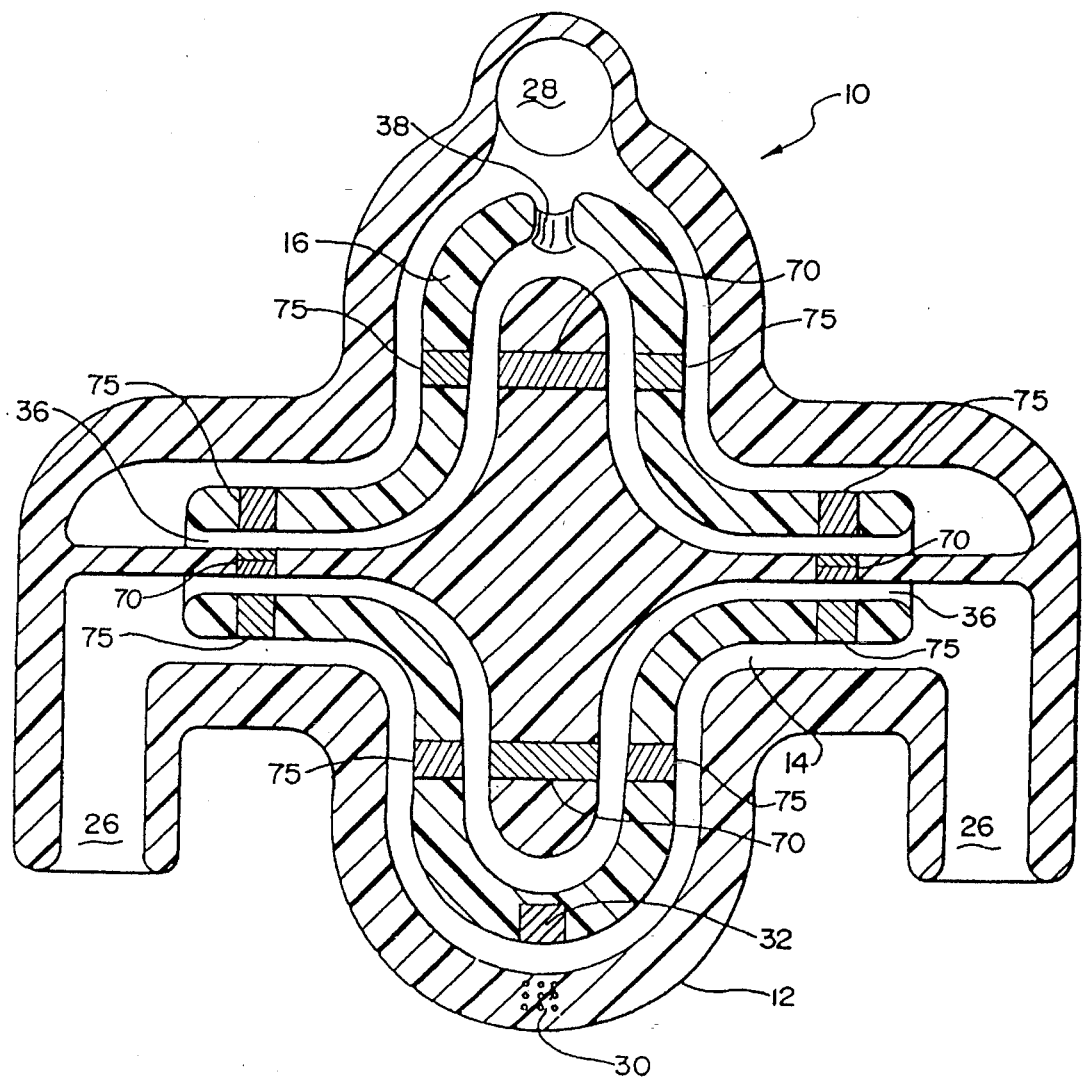
Figure 14F:
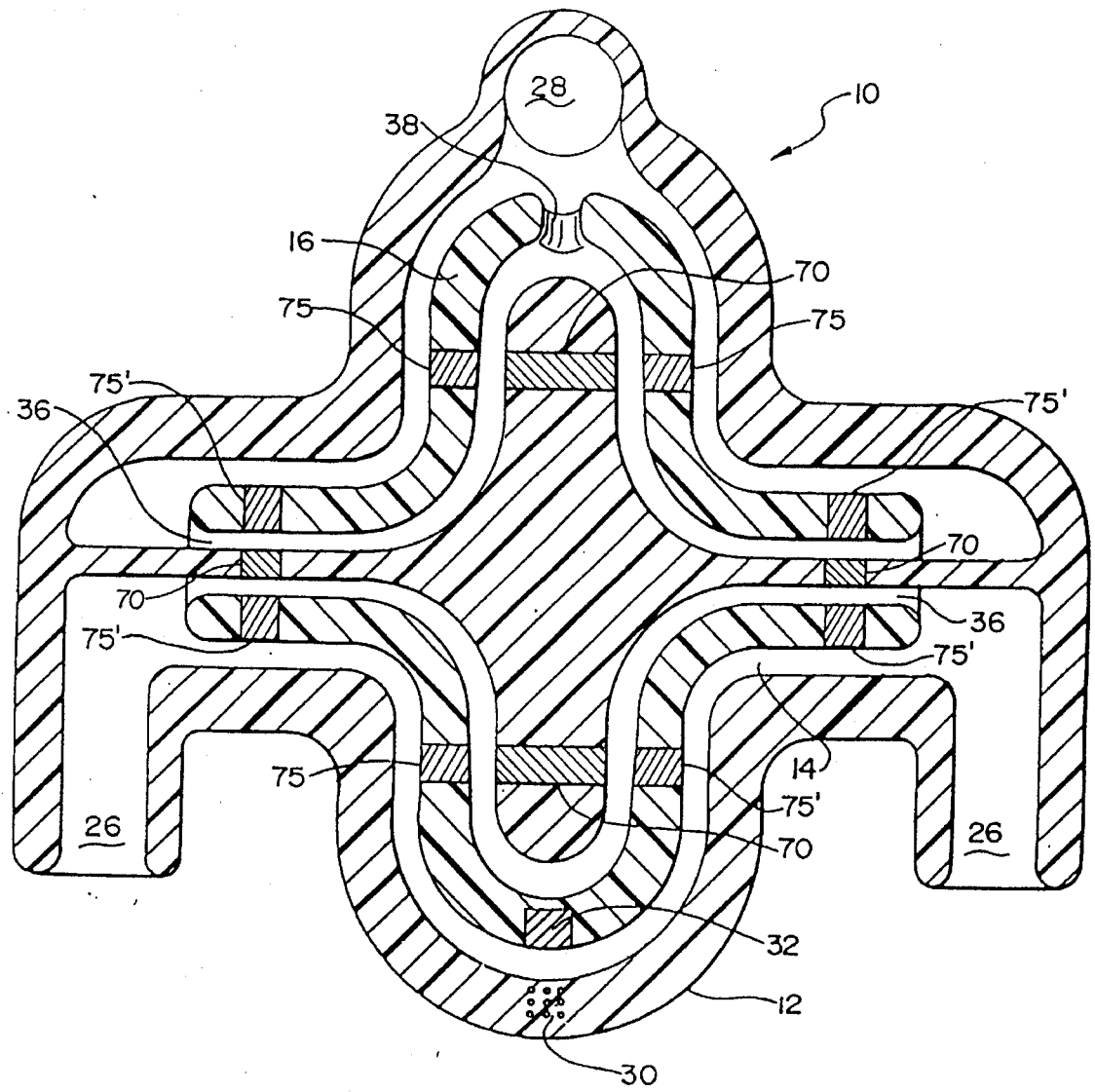
Figure 14G:
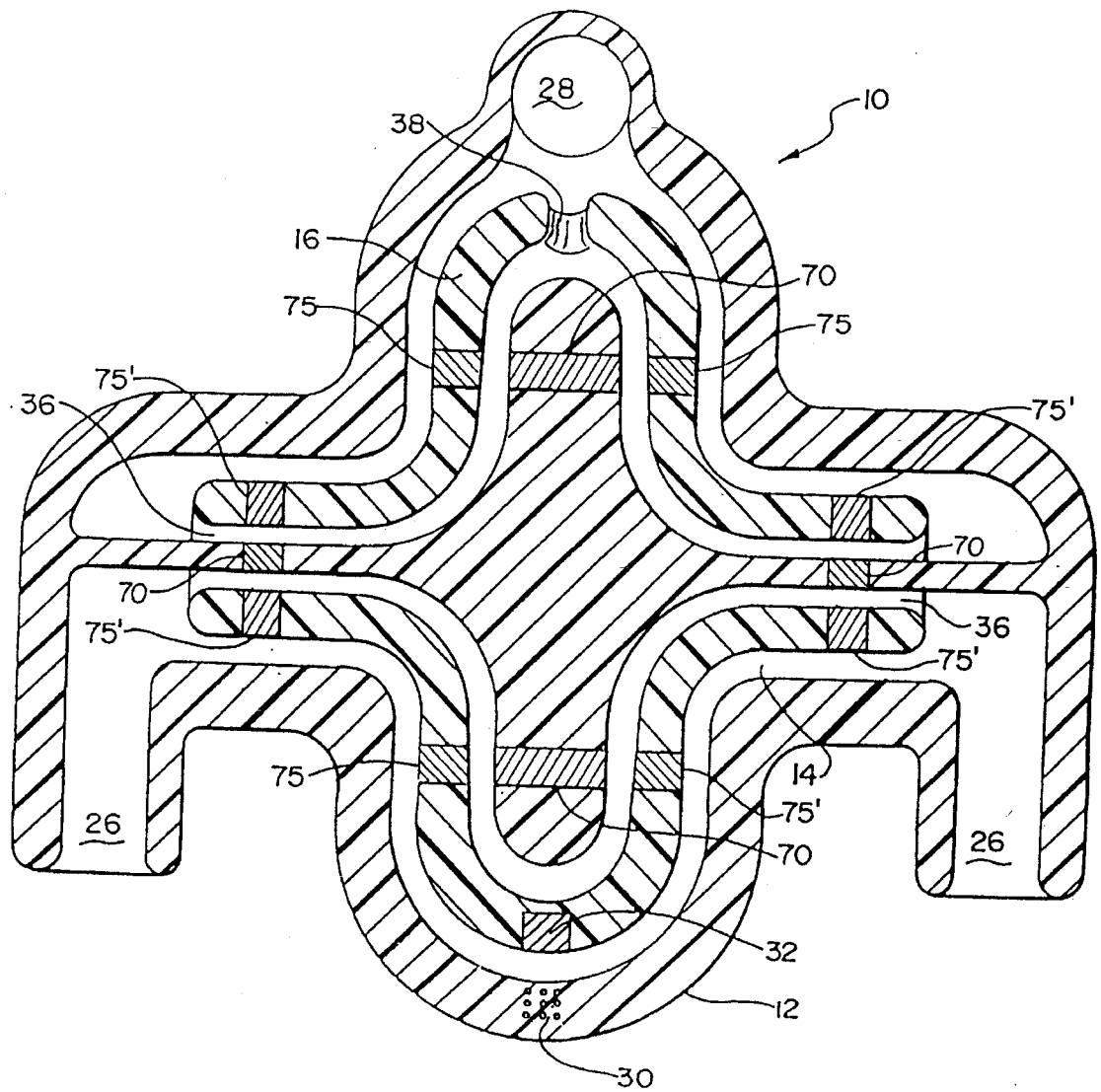
Figure 14I:
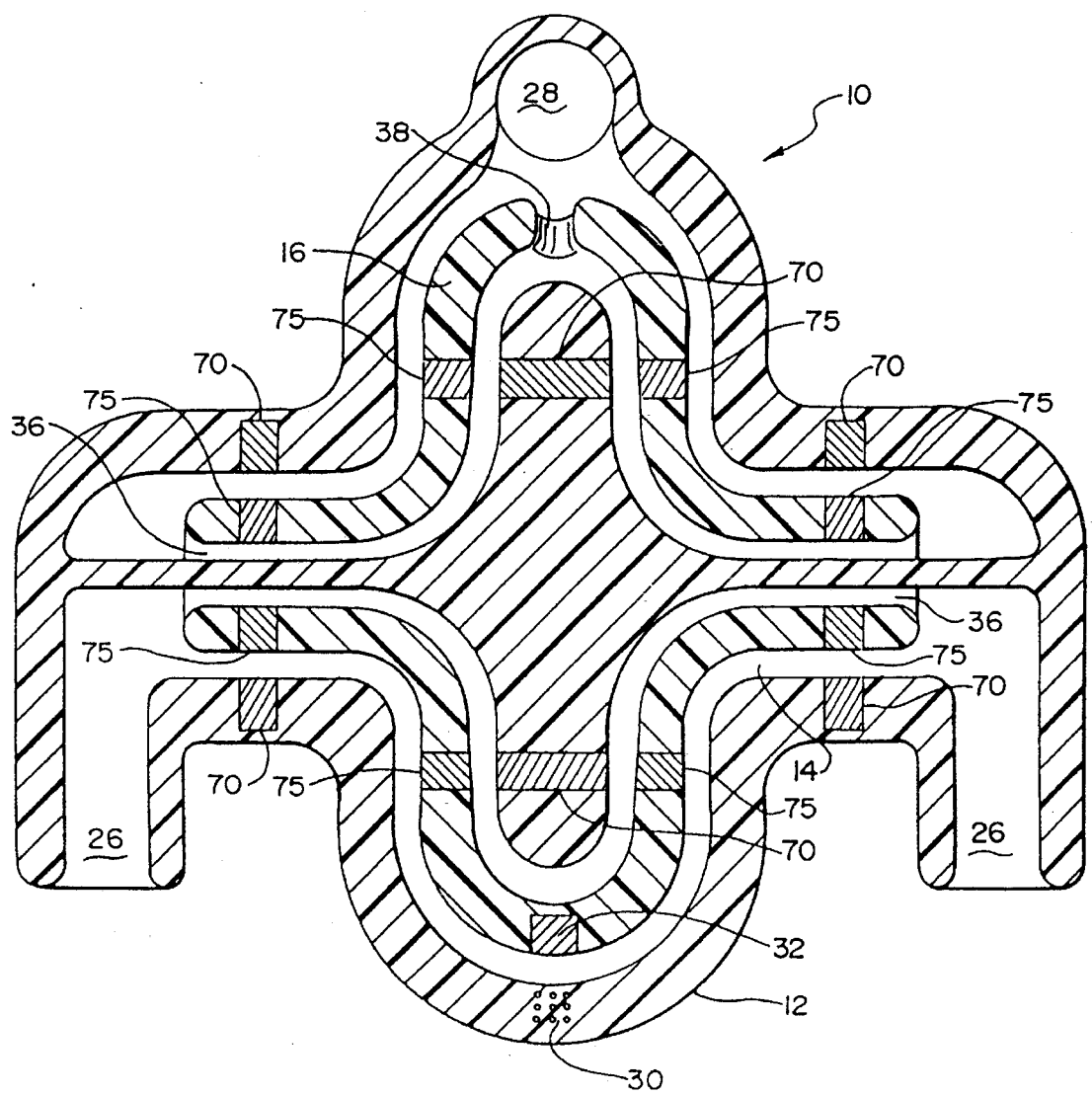
Figure 14J:
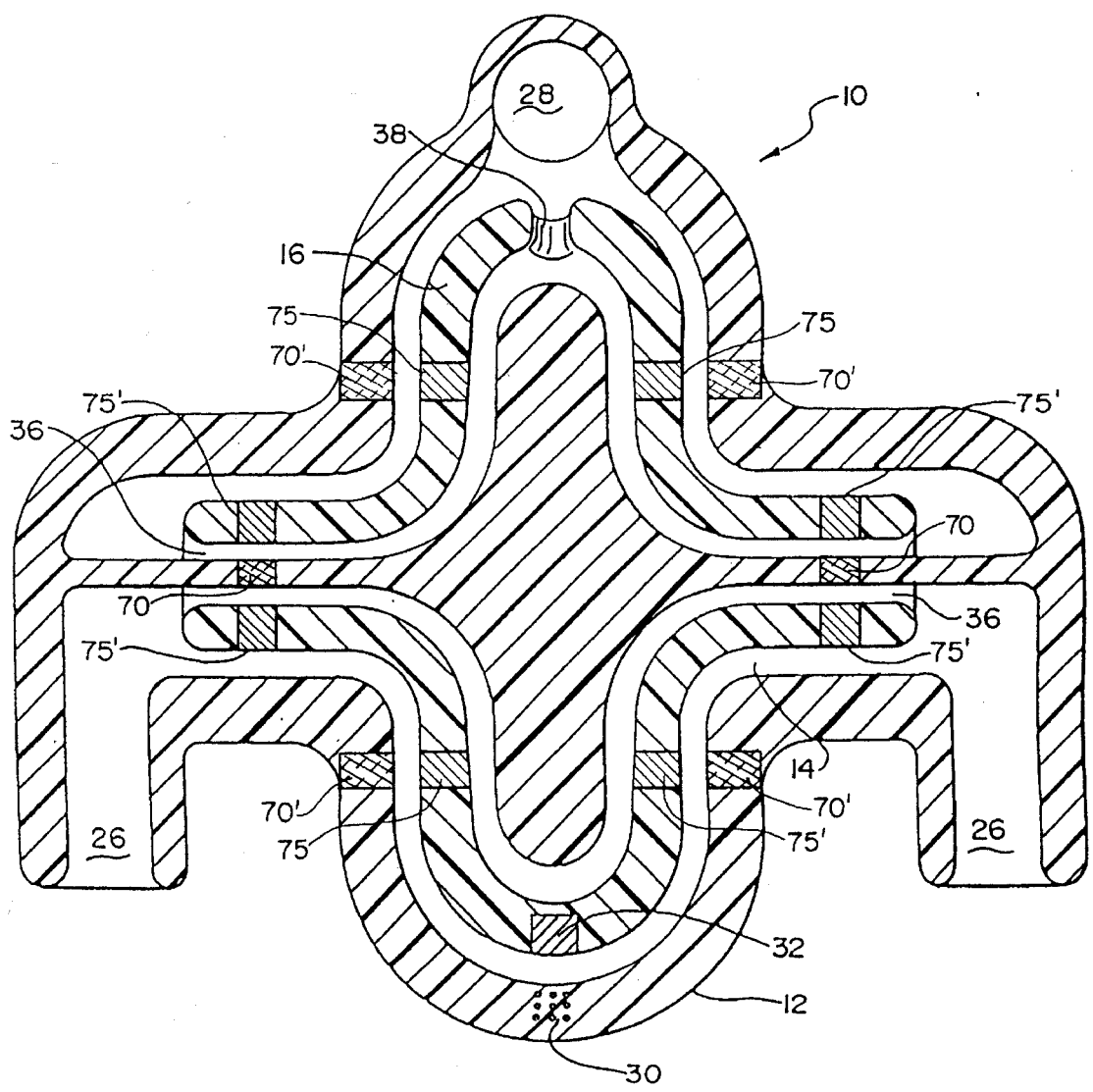
Figure 14K:
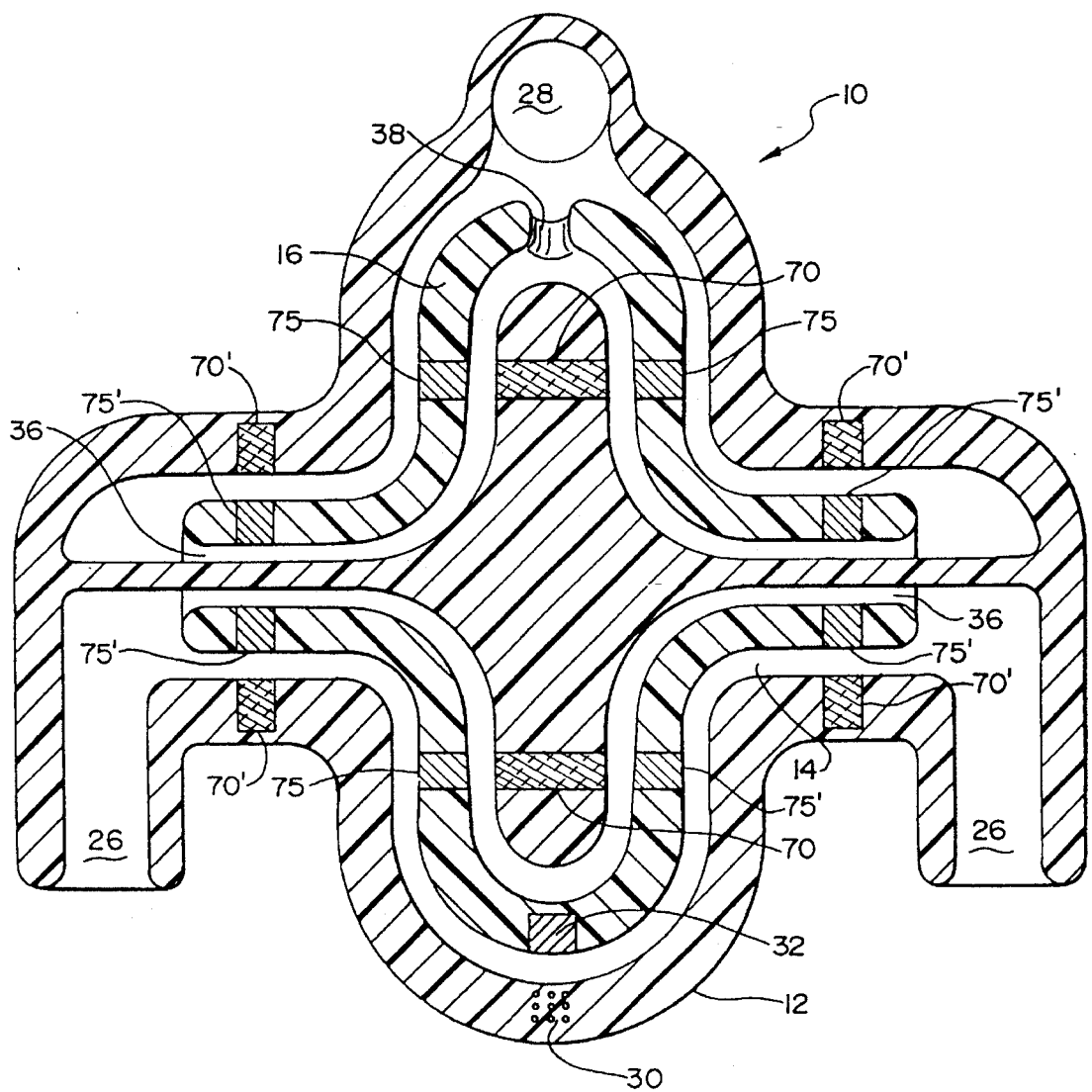
Figure 14L:
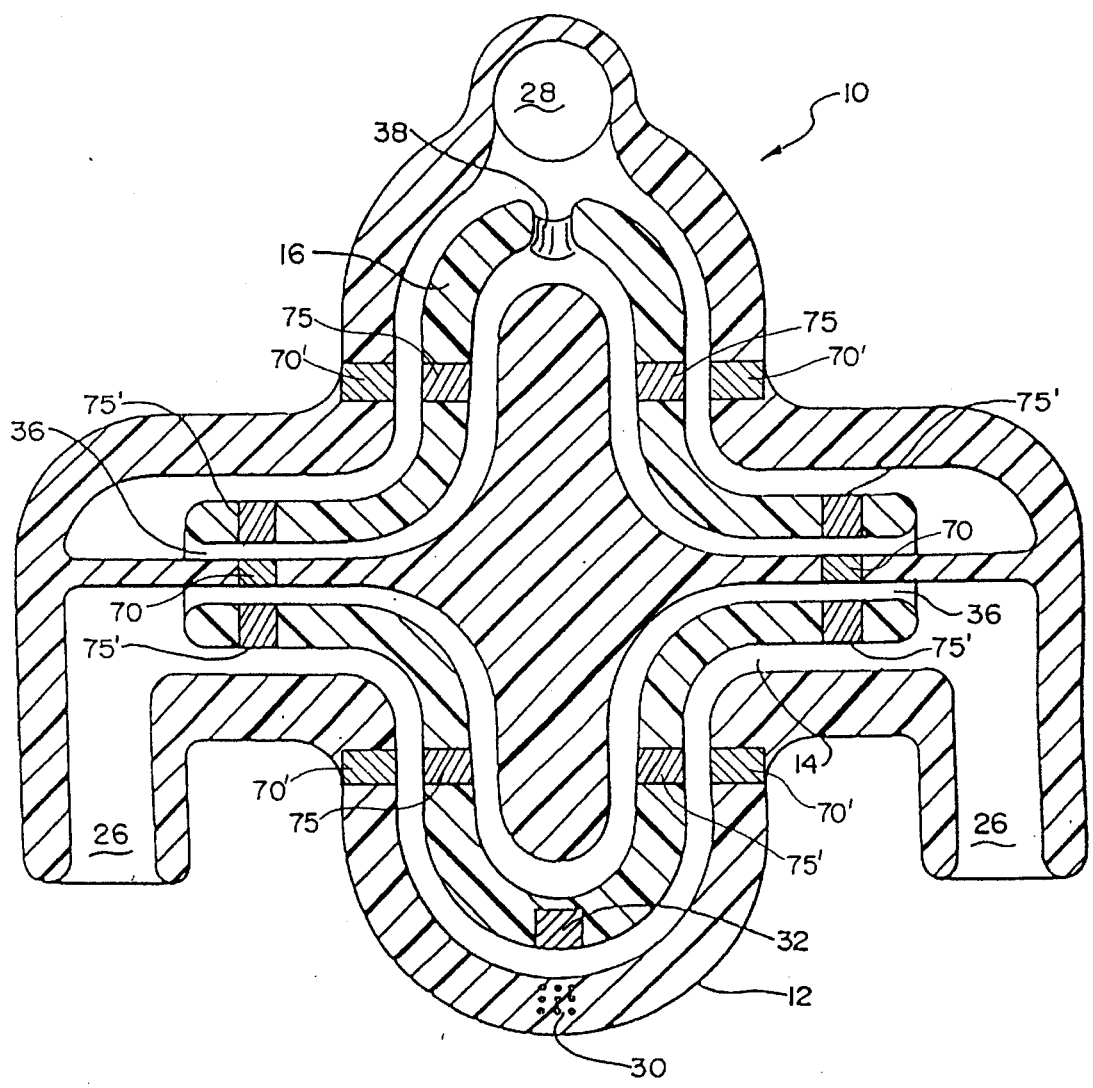
Figure 14M:
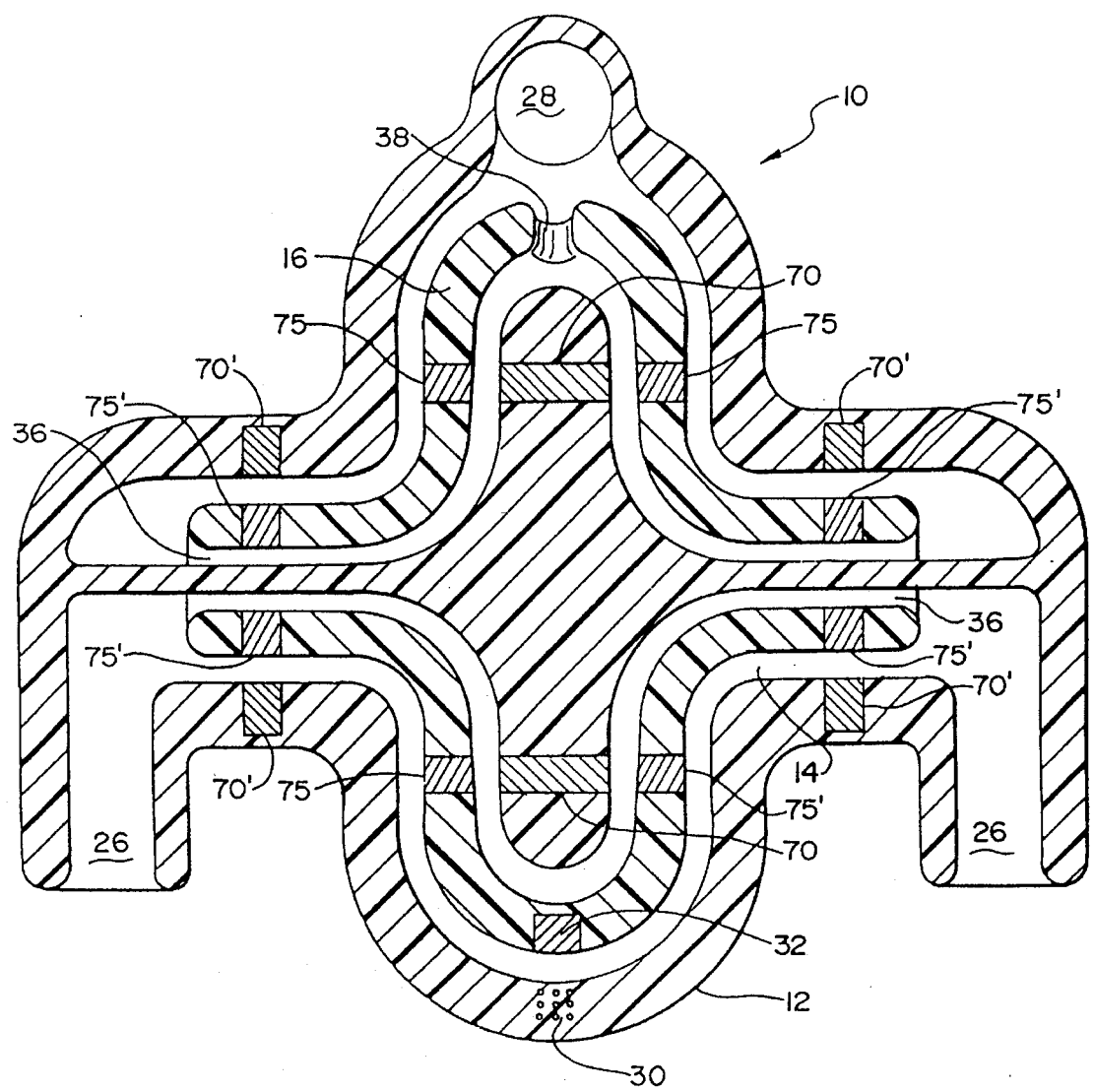

The present invention differs from the invention of the grand parent application (now U.S. Pat. No. 5,055,005) in that impeller levitation is achieved by magnetic forces in addition to fluid forces or by magnetic forces alone, and is applicable to each of the embodiments shown in U.S. Pat. No. 5,055,005, in addition to those disclosed herein. The present invention differs from the invention of the parent application (now U.S. Pat. No. 5,195,877) in that impeller levitation is achieved by a combination of diamagnets or solenoids opposed by permanent magnets, solenoids or electromagnets rather than solely by permanent magnets. Magnetic forces may be used for axial stabilization, with fluid forces being used for radial stabilization, as shown in FIG. 7; magnetic forces may be used for radial stabilization with fluid forces being used for axial stabilization, as shown in FIG. 9; or magnetic forces may be used for both radial and axial stabilization, as shown in FIGS. 1, 4, 5, 6 and 11. In addition, both magnetic and fluid forces may be used for both radial and axial stabilization, which provides a redundancy to insure operation under various adverse conditions and greater stabilization forces under ordinary conditions, as shown in FIG. 13.

Figure 8:
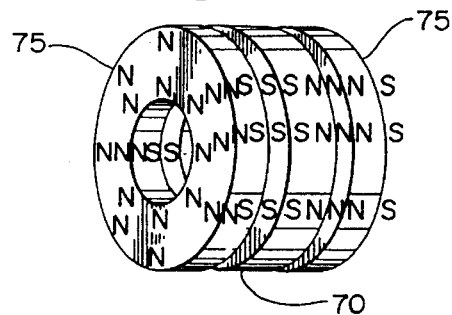
FIG. 8 is an isolated perspective view of the source of magnetic forces of FIG. 7, which are used for axial levitation.

Magnetic stabilization of impeller 16 in the axial direction is shown in FIGS. 7 and 8, in which a donut-shaped, centrally-located, magnet means 70 is mounted in central frame 62, made of non-magnetic material, which is mounted to shaft 65, which is fixed at each end to housing 12 of pump 10. Centrally located magnet 70 is thus fixed with respect to housing 12 and is enveloped by impeller 16 and is, like impeller 16, disposed with its axis coincident with axis 22. Magnet means 70 has a polarity as shown by lettering in FIG. 7, namely, its south pole is on the left, as viewed in FIG. 7, and its north pole is on the right.

A pair of surrounding magnets means 75, donut shaped and corresponding in diameter to magnet means 70, is mounted on each side of magnet means 70 for rotation with impeller 16. Magnet means 75 thus surround or oppose magnet means 70 and are disposed with their polarity opposing the polarity of magnet means 70 so that magnets means 70 and 75 repel one another.

It should be noted that impeller 16 is formed with an interior sleeve section 66, which serves as a mounting hub for rotor section 68, in which magnets 75 are embedded. Because of sleeve section 66, which extends to the outer surface of impeller 16, apertures 71 are provided in sleeve section 66 so fluid may pass from opposed inlets 36 of impeller 16, into the interior cavity thereof, and out impeller outlets 38. Impeller 16 could also be constructed without sleeve member 66 as long as a passage from inlet 36 to the interior cavity of impeller 16 is provided.

In the embodiment of FIGS. 7 and 8, the repulsive forces between magnets 70 and 75 thus result in axial stabilization of impeller 16 and fluid forces result in radial stabilization.

Figure 10:
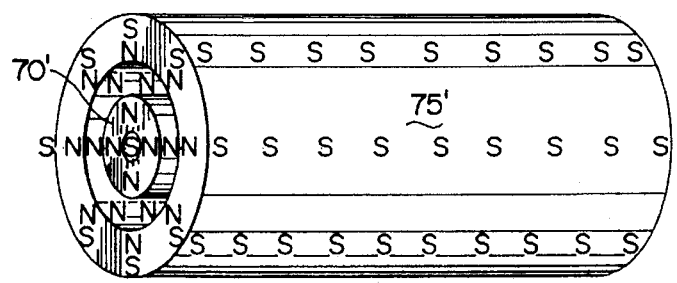
FIG. 10 is an isolated perspective view of the source of magnetic forces of FIG. 9, which are used for radial levitation.

In the embodiment of FIG. 9, radial stabilization of impeller 16 is obtained by centrally located magnet means 70', which is axially mounted on shaft 81, which is connected to housing 12 and is thus fixed with respect to housing 12. As shown in FIGS. 9 and 10, centrally located magnet means 70' is formed with a polarity such that its cylindrical surface is its north pole and its central surface as its south pole.

A surrounding cylindrical magnet means 75' is located concentrically about magnet means 70' with its interior cylindrical surface as its north pole and its exterior cylindrical surface as its south pole. Surrounding magnet means 75' is embedded in impeller 16 of non-magnetic material, which is mounted to sleeve 66 of impeller 16. Apertures 71 are provided in the embodiment of FIGS. 9 and 10 for the purpose described above in connection with the embodiment of FIGS. 7 and 8.

The repulsive magnetic forces between magnets 70' and 75' thus result in radial stabilization of impeller 16 and fluid forces result in axial stabilization.

Figure 11:
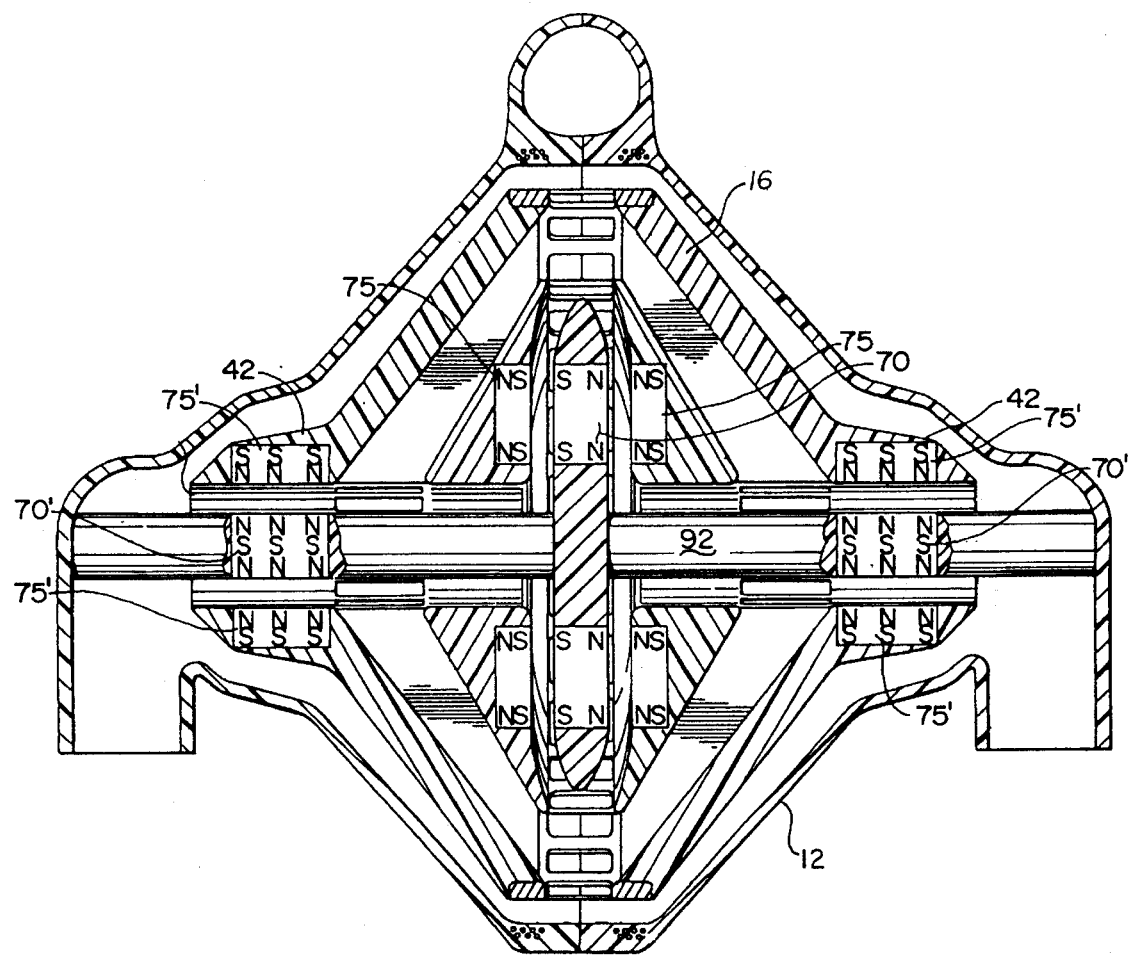
FIG. 11 is an axial sectional view of another embodiment of the present invention where both axial and radial levitation of the impeller are achieved by magnetic repulsive forces.
Figure 12:
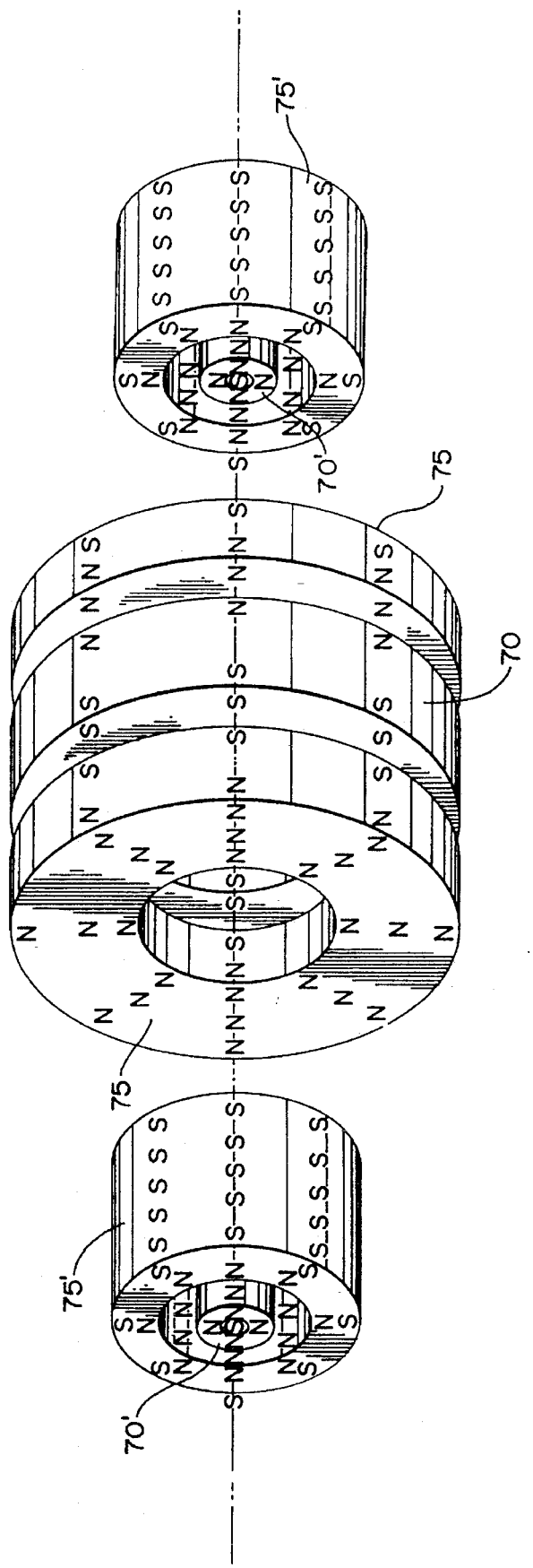
FIG. 12 is an enlarged isolated perspective view of the source of magnetic forces of FIG. 11, which are used for both axial and radial levitation.

Another embodiment in which impeller stabilization in both the axial and the radial directions is by repulsive magnetic forces is shown in FIGS. 11 and 12, in which axial stabilization is provided by magnet means 70 and 75, which are identical to the embodiment of FIGS. 7 and 8, and radial stabilization is provided by magnets 70' and 75' in a manner similar to the embodiment of FIGS. 9 and 10, except that a pair of spaced magnet sets is provided, disposed respectively at the opposed neck portions 42 of impeller 16. The two centrally located magnets 70' are mounted on shaft 92 with the exterior cylindrical surface as the north pole and the interior central surface as the south pole. The pair of cylindrical permanent magnets 75' surround each of the magnets 90 and have a south pole on the exterior cylindrical surface. The polarity of magnets 70' and 75' is therefore such that repulsive magnetic forces stabilize impeller 16 in the radial direction.

Thus, in the embodiment of FIGS. 11 and 12, impeller 16 is stabilized in both the axial and radial directions by repulsive forces between magnets 70 and 75 and magnets 70' and 75', respectively.

The embodiment shown in FIG. 13 is a combination of magnetic force stabilization in both the axial and radial directions and fluid force stabilization in both the axial and radial directions. Fluid forces are directed axially in opposed directions at each end of impeller 16 at neck portion 42 from outlet 52 of conduit 46 and, similarly, radial forces are directed in opposed directions at each end of impeller 16 at neck portion 42. Radial stabilization is also achieved by the repulsive magnetic forces between magnets 70' and 75' and axial stabilization is achieved by repulsive magnetic forces between magnets 70 and 75. The embodiment in FIG. 13 is thus redundant in that both magnetic and fluid forces combine in both the axial and radial directions. This redundancy may be of value in obtaining increased levitational or stabilizing forces and in providing a fail safe design.

Various methods may be employed to start the pumping mechanism of the present invention. The pump housing and its inlet and outlet ports, the impeller and its inlets and outlets, the conduits and fluid jet ports, and the vessels or other passageways leading to and from the pump housing may be primed with fluid prior to activation of the electromagnetic means for rotating the impeller. Fluid may be introduced into the invention at various locations from external sources. If necessary, an external pressurizing mechanism may be used to introduce an appropriate priming fluid and to expel air potentially trapped within the spaces of the invention. Once the invention has been primed, activation of the electromagnetic means may be sufficient to overcome the inertia of the impeller and to initiate rotation of the impeller. This would lead nearly immediately to generation of levitating fluid forces emanating from the fluid jet ports. As the speed of rotation of the impeller reached operating levels, the levitating fluid forces generated would bring the impeller to its operating position within the pump housing. In the case of impeller levitation in both the axial and radial directions by repulsive permanent magnetic forces, it should be recognized that levirational fluid forces generated by rotation of the impeller are not necessary.

With an impeller of a density the same as, or similar to, that of the fluid, levitating fluid forces, in the embodiments of FIGS. 7–10, will bring the impeller to its operating position very shortly after the activated electromagnetic means has induced the first several rotations of the impeller. In any case, structural constraints on displacement of the impeller from its operating position within the housing may be incorporated by those skilled in the art. For example, in the absence arrestors of the spacing between the conduit jet port structure and the impeller should be less than the spacing between the impeller and that portion of the housing encompassing the electromagnetic wire windings. Such structural constraints as described above, as well as others known to those skilled in the art, would facilitate starting of the pumping mechanism in those embodiments reliant upon fluid forces for impeller stabilization, since the impeller driving magnets would not be in a "freeze-up" contact with the electromagnetic wire windings at start-up, and movement of the impeller from its start-up position to its operating position would entail only a slight positional reorientation.

In certain applications, such as pumping human or animal blood, the surfaces of the impeller, the structure comprising the fluid jet ports, and, if present, the arresting surfaces, should be manufactured of smooth, non-magnetic materials having low coefficients of friction and low or non-thrombogenic characteristics.

As discussed earlier, the preferred application of pumps of the present invention is for pumping blood, although the invention may be used in numerous other medical and non-medical pumping applications. In human medicine, it is unknown whether or not a pulsatile blood flow is required for optimum short-term or long-term clinical efficacy of artificial blood pumps. Impeller 16 of the present; invention is most conveniently operated in a continuous, non-pulsatile mode. However, depending on the configuration and mode of operation of the electromagnetic means for driving impeller 16, the mode of operation may be pulsatile, or even intermittent. Likewise, the levitating fluid jets could be operated in a continuous, pulsatile, or intermittent mode. Alternatively, the operation of the impeller and levitating fluid jets could fluctuate between continuous, pulsatile, and intermittent modes, or between any combination of these modes, depending on the structure and intended use of specific embodiments of the present invention. Appropriate modes of operation will be obvious to those skilled in the art.

It should also be recognized that, although an advantage of the present invention is the elimination of bearings, in a pump in which the impeller is mounted in bearings the levitational forces described herein may be applied to the bearings, thereby levitating the impeller through forces applied to the bearings.

From the foregoing, it will be obvious to those skilled in the art that various modifications in the above described devices can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A fluid pump comprising:

a housing defining a pumping chamber, a pumping chamber inlet port and a pumping chamber outlet port;

a rotatable impeller disposed in said pumping chamber for rotation about an axis;

a polarized electromagnetic means associated with said impeller and said housing for rotating said impeller about said axis;

a plurality of diamagnets fixed with respect to said impeller; and a plurality of magnet means fixed with respect to said housing, disposed in magnetic communication with said plurality of diamagnets, and oriented generally axially and radially with said plurality of diamagnets to thereby stabilize said impeller in both the axial and radial directions by magnetic forces levitating said impeller.

2. The fluid pump of claim 1 wherein said magnet means is selected from the group consisting of permanent magnets, solenoids and electromagnets.

3. The fluid pump of claim 2 wherein said impeller has a density substantially equal to the density of a fluid pumped by said fluid pump.

4. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets fixed with respect to said impeller;

a plurality of magnet means fixed with respect to said central frame, in magnetic communication with said plurality of diamagnets, and oriented generally axially and radially with said plurality of diamagnets, to thereby stabilize said impeller in both the axial and radial directions by magnetic forces levitating said impeller.

5. The fluid pump of claim 4 further comprising a plurality of magnet means fixed with respect to said housing in a generally axial direction and one of diamagnets and permanent magnets fixed with respect to said impeller in a generally axial direction, whereby said impeller is provided with additional radial stability by levitating magnetic forces.

6. The fluid pump of either claim 4 or 5 wherein said magnet means are selected from the group consisting of permanent magnets, solenoids and electromagnets.

7. The fluid pump of claim 6 wherein said impeller has a density substantially equal to the density of a fluid pumped by said fluid pump.

8. A fluid pump comprising:

a housing defining a pumping chamber, a pumping chamber inlet port and a pumping chamber outlet port;

a rotatable impeller disposed in said pumping chamber for rotation about an axis;

a polarized electromagnetic means associated with said impeller and said housing for rotating said impeller about said axis;

a plurality of diamagnets fixed with respect to housing; and a plurality of permanent magnets fixed with respect to said impeller such that each said permanent magnet is disposed in magnetic communication with a diamagnet and oriented one of generally axially and radially with said diamagnet, to thereby stabilize the impeller in both the axial and radial directions by magnetic forces levitating said impeller.

9. The fluid pump of claim 8 wherein said impeller has a density substantially equal to the density of the fluid pumped by said fluid pump.

10. The fluid pump of claim 8 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

11. A fluid pump comprising:

a housing defining a pumping chamber, a pumping chamber inlet port and a pumping chamber outlet port;

a rotatable impeller disposed in said pumping chamber for rotation about an axis;

a polarized electromagnetic means associated with said impeller and said housing for rotating said impeller about said axis;

a plurality of diamagnets axially fixed with respect to said impeller and radially fixed with respect to said housing; and a plurality of permanent magnets axially fixed with respect to said housing and radially fixed with respect to said impeller, such that each said permanent magnet is disposed in magnetic communication with a diamagnet and oriented one of generally axially and radially with said diamagnet, to thereby stabilize the impeller in both the axial and radial directions by magnetic forces levitating said impeller.

12. The fluid pump of claim 11 wherein said impeller has a density substantially equal to the density of the fluid pumped by said fluid pump.

13. The fluid pump of claim 11 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

14. A fluid pump comprising:

a housing defining a pumping chamber, a pumping chamber inlet port and a pumping chamber outlet port;

a rotatable impeller disposed in said pumping chamber for rotation about an axis;

a polarized electromagnetic means associated with said impeller and said housing for rotating said impeller about said axis;

a plurality of diamagnets radially fixed with respect to said impeller and axially fixed with respect to said housing; and a plurality of permanent magnets radially fixed with respect to said housing and axially fixed with respect to said impeller, such that each said permanent magnet is disposed in magnetic communication with a diamagnet and oriented one of generally axially and radially with said diamagnet, to thereby stabilize the impeller in both the axial and radial directions by magnetic forces levitating said impeller.

15. The fluid pump of claim 14 wherein said impeller has a density substantially equal to the density of the fluid pumped by said fluid pump.

16. The fluid pump of claim 14 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

17. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets fixed with respect to said central frame; and a plurality of permanent magnets fixed with respect to said impeller, such that each said permanent magnet is disposed in magnetic communication with a diamagnet and oriented one of generally axially and radially with said diamagnet, to thereby stabilize the impeller in both the axial and radial directions by magnetic forces levitating said impeller.

18. The fluid pump of claim 17 wherein said impeller has a density substantially equal to the density of the fluid pumped by said fluid pump.

19. The fluid pump of claim 17 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

20. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets axially fixed with respect to said impeller and radially fixed with respect to said central frame; and a plurality of permanent magnets axially fixed with respect to said central frame and radially fixed with respect to said impeller, such that each said permanent magnet is disposed in magnetic communication with a diamagnet and oriented one of generally axially and radially with said diamagnet, to thereby stabilize the impeller in both the axial and radial directions by magnetic forces levitating said impeller.

21. The fluid pump of claim 20 wherein said impeller has a density substantially equal to the density of the fluid pumped by said fluid pump.

22. The fluid pump of claim 20 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

23. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets radially fixed with respect to said impeller and axially fixed with respect to said central frame; and a plurality of permanent magnets radially fixed with respect to said central frame and axially fixed with respect to said impeller, such that each said permanent magnet is disposed in magnetic communication with a diamagnet and oriented one of generally axially and radially with said diamagnet, to thereby stabilize the impeller in both the axial and radial directions by magnetic forces levitating said impeller.

24. The fluid pump of claim 23 wherein said impeller has a density substantially equal to the density of the fluid pumped by said fluid pump.

25. The fluid pump of claim 23 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

26. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets fixed with respect to said impeller; and a plurality of magnet means radially fixed with respect to said central frame and axially fixed with respect to said housing, such that each said permanent magnet is disposed in magnetic communication with a diamagnet and oriented one of generally axially and radially with said diamagnet, to thereby stabilize the impeller in both the axial and radial directions by magnetic forces levitating said impeller.

27. The fluid pump of claim 26 wherein said impeller has a density substantially equal to the density of the fluid pumped by said fluid pump.

28. The fluid pump of claim 26 further comprising means at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

29. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of diamagnets fixed with respect to said impeller; and a plurality of magnet means axially fixed with respect to said central frame and radially fixed with respect to said housing, such that each said permanent magnet is disposed in magnetic communication with a diamagnet and oriented one of generally axially and radially with said diamagnet, to thereby stabilize the impeller in both the axial and radial directions by magnetic forces levitating said impeller.

30. The fluid pump of claim 29 wherein said impeller has a density substantially equal to the density of the fluid pumped by said fluid pump.

31. The fluid pump of claim 29 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

32. A fluid pump comprising:

a housing defining a pumping chamber, a pumping chamber inlet port and a pumping chamber outlet port;

a central frame fixed with respect to said housing and disposed in said pumping chamber;

a rotatable impeller disposed in said pumping chamber for rotation about an axis about said central frame;

a polarized electromagnetic means associated with said housing and said impeller for rotating said impeller about said central frame;

a plurality of permanent magnets fixed with respect to said impeller; and a plurality of diamagnets radially fixed with respect to said central frame and axially fixed with respect to said housing, such that each said permanent magnet is disposed in magnetic communication with a diamagnet and oriented one of generally axially and radially with said diamagnet, to thereby stabilize the impeller in both the axial and radial directions by magnetic forces levitating said impeller.

33. The fluid pump of claim 32 wherein said impeller has a density substantially equal to the density of the fluid pumped by said fluid pump.

34. The fluid pump of claim 32 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

35. A fluid pump comprising:
   a housing defining a pumping chamber, a pumping chamber inlet port and a pumping chamber outlet port;
   a central frame fixed with respect to said housing and disposed in said pumping chamber;
   a rotatable impeller disposed in said pumping chamber for rotation about an axis about said central frame;
   a polarized electromagnetic means associated with said housing and said impeller for rotating said impeller about said central frame;
   a plurality of permanent magnets fixed with respect to said impeller; and
   a plurality of diamagnets axially fixed with respect to said central frame and radially fixed with respect to said housing, such that each said permanent magnet is disposed in magnetic communication with a diamagnet and oriented one of generally axially and radially with said diamagnet, to thereby stabilize the impeller in both the axial and radial directions by magnetic forces levitating said impeller.

36. The fluid pump of claim 35 wherein said impeller has a density substantially equal to the density of the fluid pumped by said fluid pump.

37. The fluid pump of claim 35 further comprising at least one of means for conducting fluid from the peripheral region of the impeller and discharging the fluid in opposed radial directions toward the impeller and means for conducting fluid from the peripheral region of the impeller and discharging the fluid in opposed axial directions toward the impeller, whereby said impeller is levitated in at least one of said axial and radial directions by the fluid forces.

* * * * *

(12) EX PARTE REEXAMINATION CERTIFICATE (10587th)
United States Patent
Kletschka

(10) Number: US 5,470,208 C1
(45) Certificate Issued: May 6, 2015

(54) FLUID PUMP WITH MAGNETICALLY LEVITATED IMPELLER

(76) Inventor: Harold D. Kletschka, Minneapolis, MN (US)

Reexamination Request:
No. 90/012,610, Sep. 14, 2012

Reexamination Certificate for:
Patent No.: 5,470,208
Issued: Nov. 28, 1995
Appl. No.: 07/990,985
Filed: Dec. 16, 1992

Related U.S. Application Data

(63) Continuation-in-part of application No. 07/774,034, filed on Oct. 7, 1991, now Pat. No. 5,195,877, which is a continuation-in-part of application No. 07/593,695, filed on Oct. 5, 1990, now Pat. No. 5,055,005.

(51) Int. Cl.
| | |
|---|---|
| *F04D 29/04* | (2006.01) |
| *A61M 1/10* | (2006.01) |
| *F04D 13/06* | (2006.01) |
| *F04D 29/42* | (2006.01) |
| *F04D 5/00* | (2006.01) |
| *F04D 29/18* | (2006.01) |
| *F04D 29/44* | (2006.01) |
| *H02K 7/09* | (2006.01) |
| *H02K 21/14* | (2006.01) |
| *H02K 7/14* | (2006.01) |
| *F04D 29/048* | (2006.01) |
| *F16C 32/04* | (2006.01) |

(52) U.S. Cl.
CPC ............ *A61M 1/101* (2013.01); *F05B 2240/11* (2013.01); *F04D 13/06* (2013.01); *F04D 29/048* (2013.01); *F04D 29/426* (2013.01); *H02K 21/14* (2013.01); *F16C 32/0423* (2013.01); *F04D 13/0646* (2013.01); *A61M 1/1036* (2014.01); *A61M 1/1017* (2014.01); *A61M 1/1015* (2014.01); *F04D 29/186* (2013.01); *H02K 7/09* (2013.01); *F04D 5/001* (2013.01); *F04D 29/445* (2013.01); *H02K 7/14* (2013.01); *F05B 2240/515* (2013.01); *Y10S 415/90* (2013.01)

(58) Field of Classification Search
None
See application file for complete search history.

(56) References Cited

To view the complete listing of prior art documents cited during the proceeding for Reexamination Control Number 90/012,610, please refer to the USPTO's public Patent Application Information Retrieval (PAIR) system under the Display References tab.

*Primary Examiner* — William Doerrler

(57) ABSTRACT

A fluid pump with a rotary impeller is disclosed which comprises an electromagnetically-driven, bearing-free, seal-free rotary impeller levitated by localized opposed, magnetic forces and by fluid forces, or by localized opposed magnetic forces only. Levitation by localized opposed magnetic forces alone or by a combination of magnetic and fluid forces of an impeller driven by electromagnetic forces eliminates the need for bearings and seals in the driving mechanism. This avoids the heat build-up and leakage associated with other pumping mechanisms, which can be of importance in pumping of physiological fluids such as blood. The levitating forces of the present invention are applied both axially and radially with respect to the impeller. The magnetic forces are provided by a combination of diamagnets or solenoids, opposed by permanent magnets, solenoids or electromagnets. The invention should be of use in numerous medical and non-medical applications where the benefits of impeller levitation by localized forces are apparent.

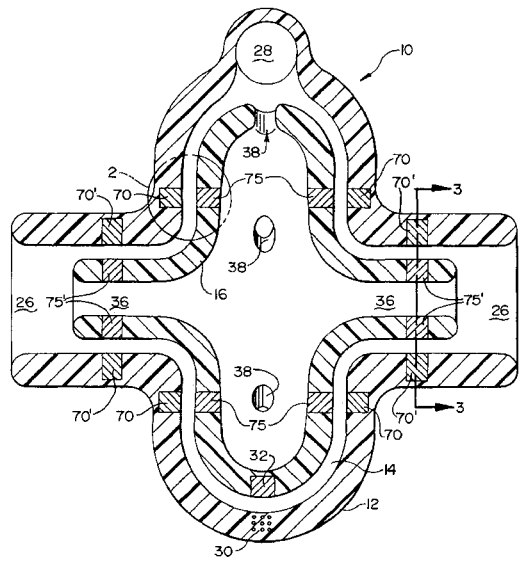

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1, 8, 11 and 14 are cancelled.

Claims 2-7, 9, 10, 12, 13 and 15-37 were not reexamined.

* * * * *